(12) United States Patent
Wakita et al.

(10) Patent No.: US 9,316,595 B2
(45) Date of Patent: Apr. 19, 2016

(54) METHOD FOR OUTPUTTING FRESHNESS INFORMATION, FRESHNESS INFORMATION OUTPUT APPARATUS, AND NON-TRANSITORY COMPUTER-READABLE RECORDING MEDIUM

(71) Applicant: Panasonic Corporation, Osaka (JP)

(72) Inventors: Yumi Wakita, Nara (JP); Jun Ozawa, Nara (JP); Naoshi Kondo, Kyoto (JP); Yuuichi Ogawa, Kyoto (JP); Tetsuhito Suzuki, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/626,841

(22) Filed: Feb. 19, 2015

(65) Prior Publication Data
US 2015/0247807 A1  Sep. 3, 2015

(30) Foreign Application Priority Data

Feb. 28, 2014 (JP) .................. 2014-039572

(51) Int. Cl.
*G01J 5/02* (2006.01)
*G01N 21/84* (2006.01)
*G01N 33/12* (2006.01)
*G01N 21/33* (2006.01)
*G01N 21/35* (2014.01)

(52) U.S. Cl.
CPC ............... *G01N 21/84* (2013.01); *G01N 21/33* (2013.01); *G01N 21/35* (2013.01); *G01N 33/12* (2013.01); *G01N 2201/0221* (2013.01)

(58) Field of Classification Search
CPC ............................ G01N 21/3563; A22C 25/00
See application file for complete search history.

(56) References Cited

U.S. PATENT DOCUMENTS

2013/0062523 A1 * 3/2013 Chernokalskaya et al. ................. 250/339.07

FOREIGN PATENT DOCUMENTS

| CN | 102217668 B | * | 1/2013 |
| JP | 2007-292512 | | 11/2007 |
| JP | 2010-286262 | | 12/2010 |

OTHER PUBLICATIONS

Feng et al., "Fish freshness rapid detection based on fish-eye image," 2013, Proceedings of SPIE, vol. 8761, pp. 87610A-1 to 87610A-5.*
Itoh et al., "Droplet-based microfluidic sensing system for rapid fish freshness determination," 2012, Sensors and Actuators B, vol. 171-172, pp. 619-626.*

* cited by examiner

Primary Examiner — Kiho Kim
(74) Attorney, Agent, or Firm — Wenderoth, Lind & Ponack, L.L.P.

(57) ABSTRACT

In a method for outputting freshness information used by a freshness information output apparatus, ultraviolet light is radiated onto an eye of a fish, an ultraviolet image of the eye of the fish is captured using an ultraviolet camera, a computer analyzes the ultraviolet image to determine freshness of a fish on the basis of luminance of an iris portion of the eye of the fish, and freshness information indicating the freshness of the fish is output to a display.

12 Claims, 20 Drawing Sheets

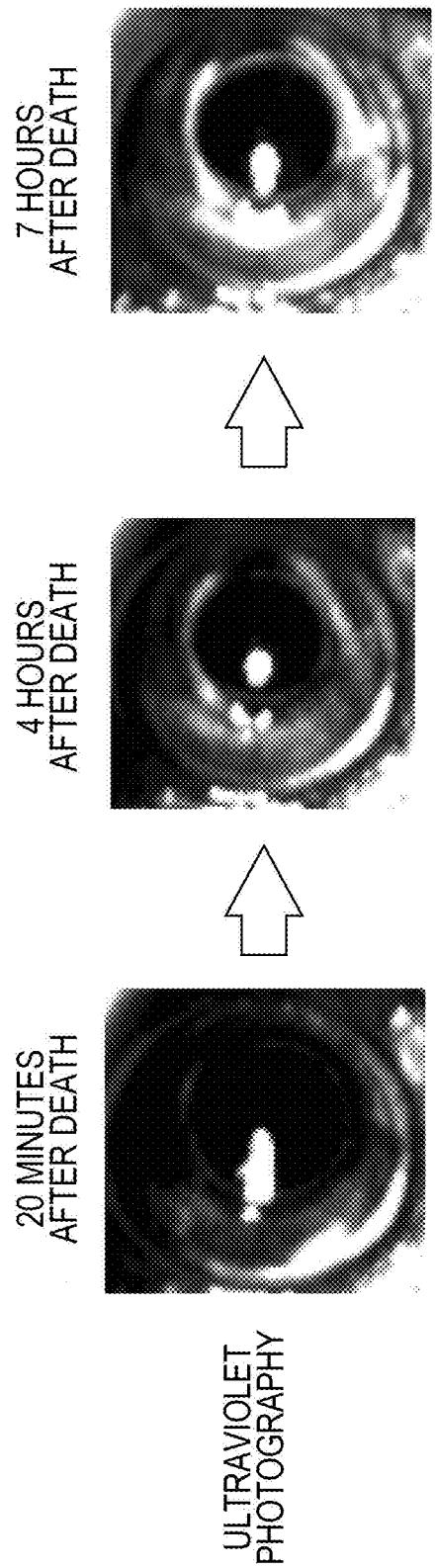

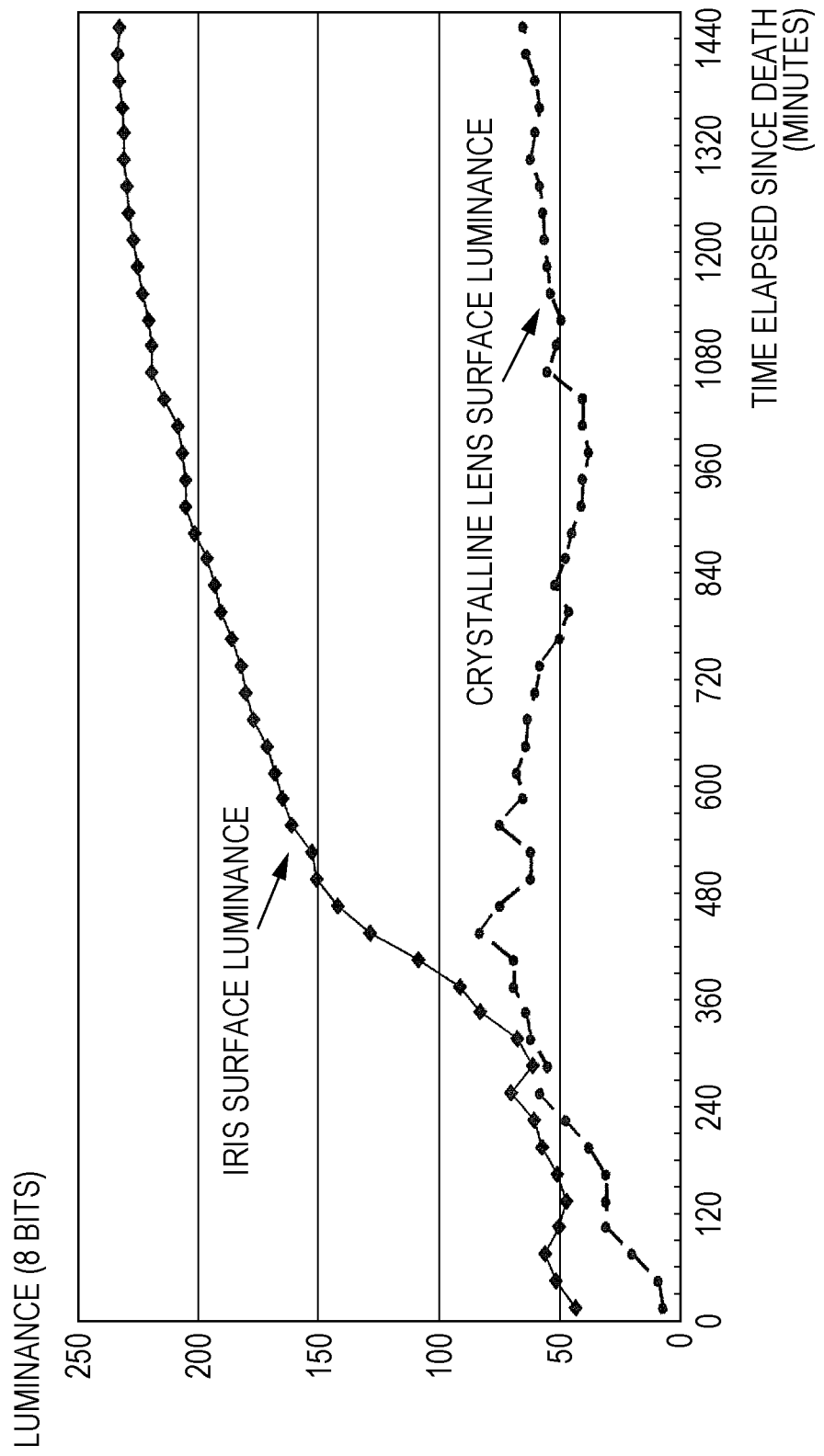

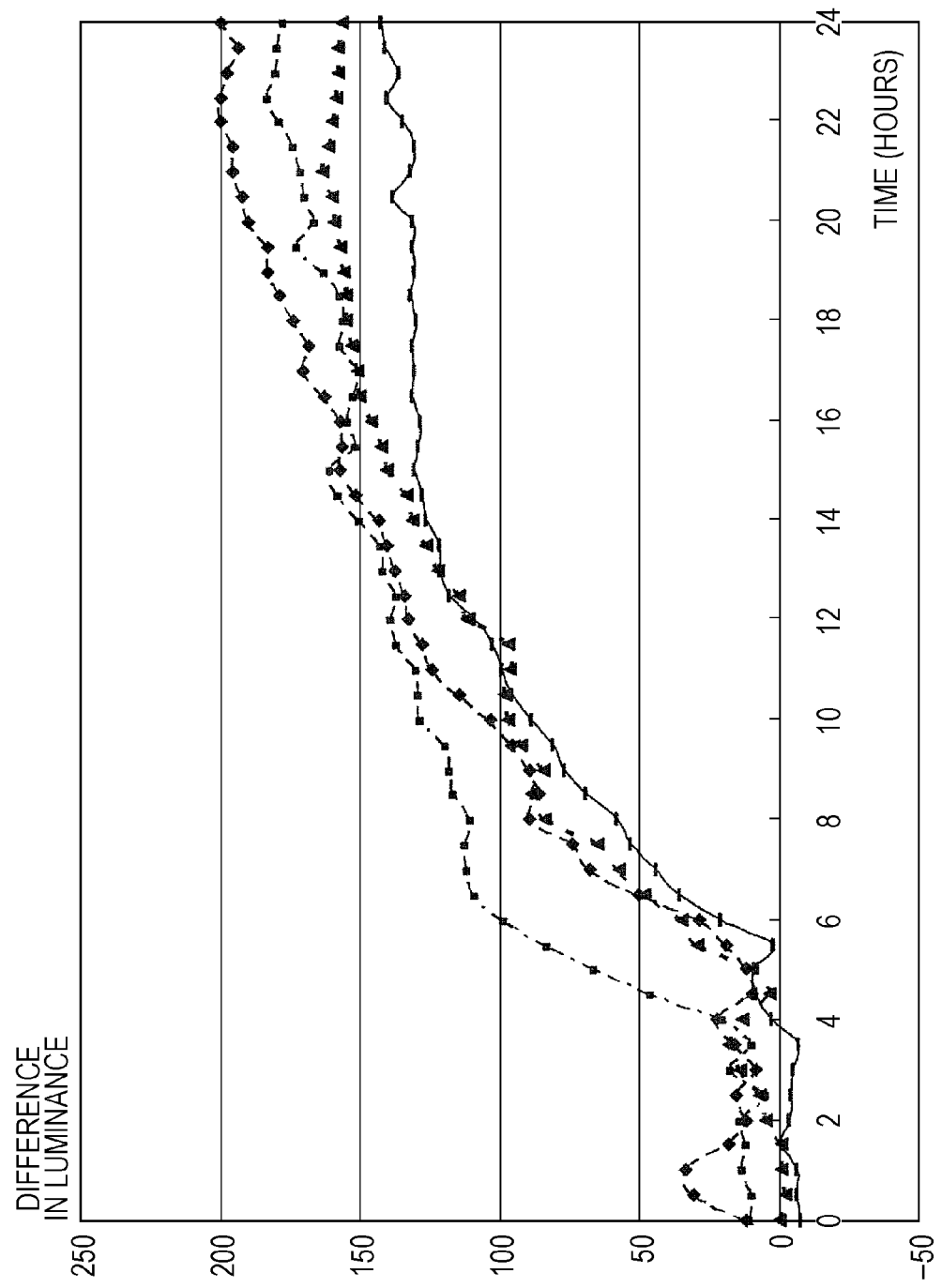

FIG. 9A

| FRESHNESS INDEX A (DIFFERENCE IN LUMINANCE) | TIME ELAPSED SINCE DEATH |
|---|---|
| 100 OR SMALLER | SHORTER THAN 6 HOURS |
| 101 TO 130 | 6 HOURS OR LONGER BUT SHORTER THAN 12 HOURS |
| 131 TO 180 | 12 HOURS OR LONGER BUT SHORTER THAN 18 HOURS |

FIG. 9B

| FRESHNESS INDEX A (DIFFERENCE IN LUMINANCE) | ESTIMATED TIME ELAPSED SINCE DEATH | FRESHNESS |
|---|---|---|
| 100 OR SMALLER | SHORTER THAN 6 HOURS | VERY FRESH (EDIBLE RAW) |
| 101 TO 130 | 6 HOURS OR LONGER BUT SHORTER THAN 12 HOURS | FRESH (INEDIBLE RAW) |
| 131 TO 180 | 12 HOURS OR LONGER BUT SHORTER THAN 18 HOURS | STILL FRESH (INEDIBLE RAW) |
| ... | ... | NOT FRESH (INEDIBLE) |

FIG. 10A
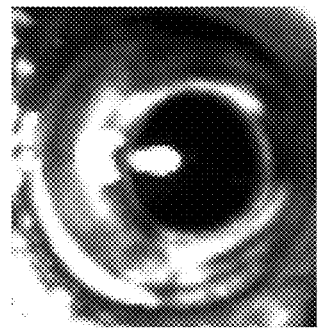
DERIVATIVE
FILTERING PROCESS
7 HOURS AFTER DEATH
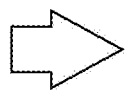
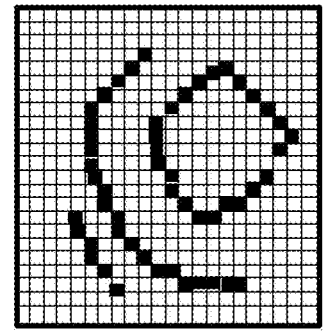
DERIVATIVE
FILTERING PROCESS
FIG. 10B
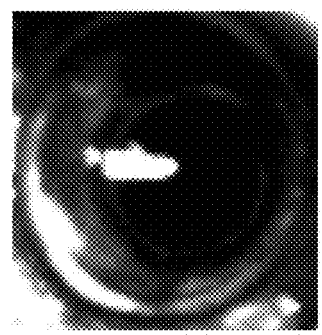
20 MINUTES AFTER DEATH
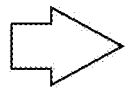
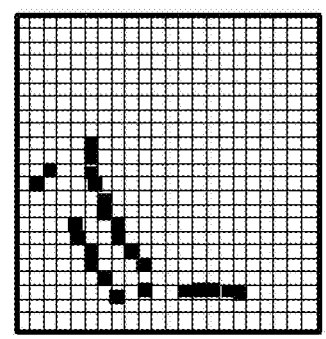
DERIVATIVE
FILTERING PROCESS

FIG. 22A

| FRESHNESS INDEX B (DIFFERENCE IN LUMINANCE) | TIME ELAPSED SINCE DEATH |
|---|---|
| 30 OR SMALLER | SHORTER THAN 8 HOURS |
| 31 TO 80 | 8 HOURS OR LONGER BUT SHORTER THAN 14 HOURS |
| 81 TO 120 | 14 HOURS OR LONGER BUT SHORTER THAN 24 HOURS |

FIG. 22B

| FRESHNESS INDEX B (DIFFERENCE IN LUMINANCE) | ESTIMATED TIME ELAPSED SINCE DEATH | FRESHNESS |
|---|---|---|
| 30 OR SMALLER | SHORTER THAN 8 HOURS | VERY FRESH (EDIBLE RAW) |
| 31 TO 80 | 8 HOURS OR LONGER BUT SHORTER THAN 14 HOURS | FRESH (INEDIBLE RAW) |
| 81 TO 120 | 14 HOURS OR LONGER BUT SHORTER THAN 24 HOURS | STILL FRESH (INEDIBLE RAW) |
| ... | ... | NOT FRESH (INEDIBLE) |

METHOD FOR OUTPUTTING FRESHNESS INFORMATION, FRESHNESS INFORMATION OUTPUT APPARATUS, AND NON-TRANSITORY COMPUTER-READABLE RECORDING MEDIUM

BACKGROUND

1. Technical Field

The present disclosure relates to a method for outputting freshness information, a freshness information output apparatus, and a non-transitory computer-readable recording medium used for outputting freshness information regarding a fish.

2. Description of the Related Art

In general, when the freshness of a fish is determined, an expert visually checks the appearance of the fish and the state of its surface and determines the freshness of the fish on the basis of color, luster, the state of scales, and the like. This method, however, depends heavily on the personal opinion of the expert. Therefore, a quantitative method, which can provide more objective evaluation, is desired.

As one of quantitative methods, a method in which an index K is measured is known. After a fish dies, related enzymes decompose adenosine triphosphate (ATP) in the fish's muscle in the following process.

Decomposition process: ATP→adenosine diphosphate (ADP)→adenosine monophosphate (AMP)→inosine monophosphate (IMP)→inosine (HxR)→hypoxanthine (Hx)

This decomposition process is the same in any kind of fish. As a fish deteriorates, ATP decreases and more inosinic acids and hypoxanthine are generated. The index K is defined as a ratio of the amount of inosinic acids and hypoxanthine to the total amount of the above-mentioned substances.

Because measurement of the amount of each substance for obtaining the index K involves chemical reactions, a lot of advance preparation is needed, and it takes time to complete the chemical reactions. In addition, part of the fish needs to be cut off before initiating the chemical reactions.

Since fish will be put on the table, a method for non-invasively evaluating the freshness of a fish, that is, a method that does not involve chemical reactions, is more desirable from a hygiene perspective.

As methods for evaluating freshness that do not involve chemical reactions, for example, a method for determining the freshness of a piece of meat by radiating polarized infrared rays onto tissues of the piece of meat and detecting the light intensity distribution of the polarization angle of transmitted or reflected light is disclosed as an example of the related art (Japanese Patent No. 4806285). In addition, a method in which near-infrared light having a stripe pattern in which bright portions and dark portions are alternately arranged is radiated onto a relatively transparent fish or shellfish and the freshness of the fish or the shellfish is determined using a contrast value of obtained image data having a stripe pattern is disclosed (Japanese Unexamined Patent Application Publication No. 2010-286262). Since these methods do not involve chemical reactions, freshness can be determined in a short period of time.

SUMMARY

The method disclosed in Japanese Patent No. 4806285, however, is effective only when a fish has been filleted like a piece of meat, and the method disclosed in Japanese Unexamined Patent Application Publication No. 2010-286262 is effective only when a fish is relatively transparent. These methods can not necessarily be used in evaluation of the freshness of any kind of fish.

One non-limiting and exemplary embodiment provides, in order to satisfy demand for a method for evaluating the freshness of a whole fish and a method for evaluating the freshness of a fish that is not so transparent, a method for outputting, using a different procedure than before, freshness information regarding a fish in a short period of time without invading the fish.

In one general aspect, the techniques disclosed here feature a method for obtaining information indicating the luminance of an iris portion of an eye of a fish onto which ultraviolet light has been radiated and outputting freshness information indicating the freshness of the fish on the basis of the foregoing information.

According to the present disclosure, freshness information regarding a fish can be output in a short period of time without invading the fish.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or disadvantages.

BRIEF DESCRIPTION OF THE DRAWINGS

FIG. 6 is a diagram illustrating images of an eye of a fish captured by an ultraviolet camera;

FIG. 7 is a graph illustrating temporal changes in the luminance of an iris portion and a crystalline lens portion of an eye of a fish;

FIG. 8 is a graph illustrating temporal changes in a difference between the average luminance values of the iris portion and the crystalline lens portion of each of a plurality of fish;

FIG. 9A is a table in which the ranges of values of a freshness index A and time elapsed since death at room temperature are associated with each other;

FIG. 9B is a table in which the ranges of values of the freshness index A and information indicating the degree of freshness are associated with each other;

FIGS. 10A and 10B are diagrams illustrating states in which a first derivative filter is applied to an ultraviolet image of an eye of a fish;

FIG. 22A is a table in which the ranges of values of a freshness index B and time elapsed since death at room temperature are associated with each other;

FIG. 22B is a table in which the ranges of values of the freshness index B and information indicating the degree of freshness are associated with each other.

DETAILED DESCRIPTION

Figure 1:
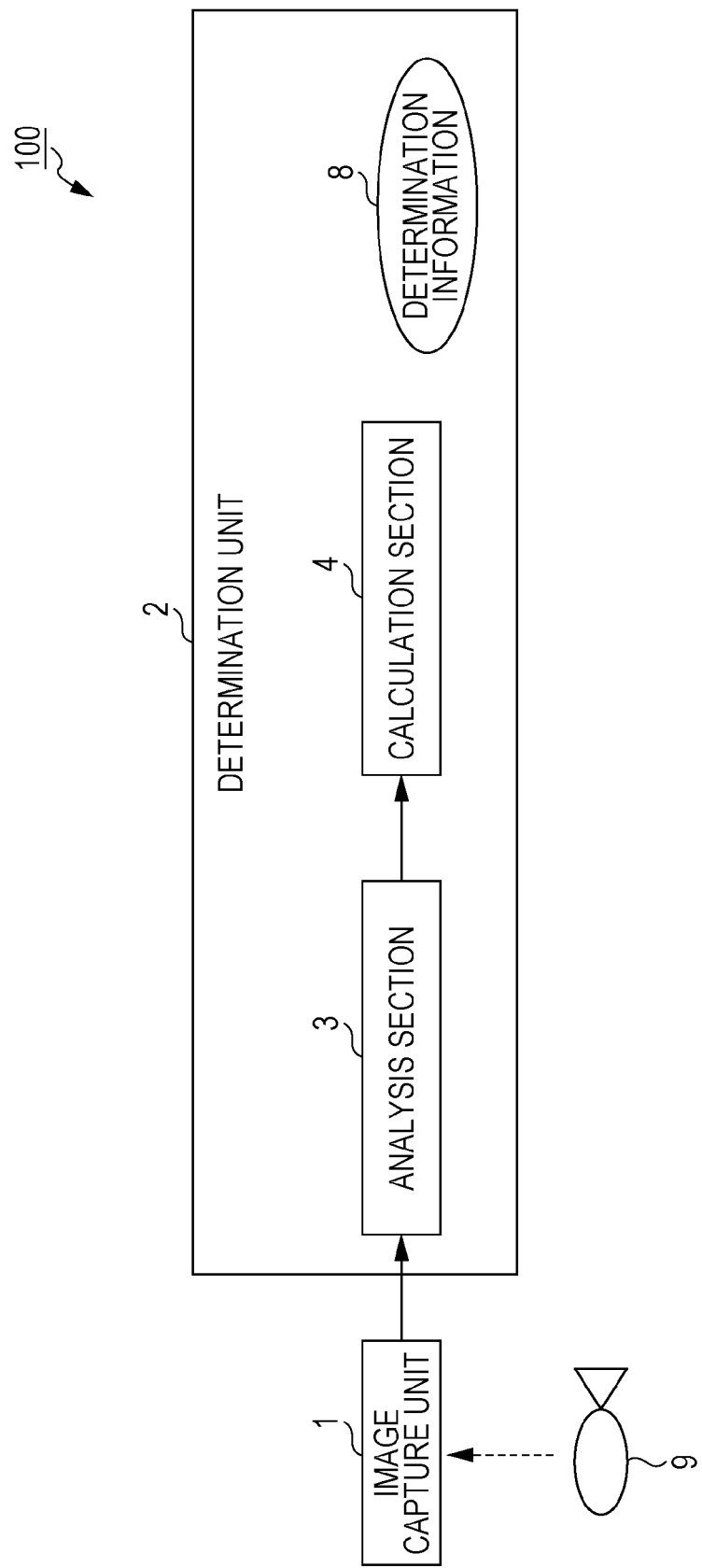
FIG. 1 is a functional block diagram illustrating a freshness information output apparatus according to a first embodiment.

A method for outputting freshness information according to the present disclosure, in which, unlike the examples of the related art, temporal changes in the luminance (luminance in an ultraviolet range) of an iris portion of an eye of a fish are focused upon in order to output the freshness information regarding the fish in a short period of time without invading the fish, is a method for outputting freshness information including the steps of obtaining information indicating luminance of an iris portion of an eye of a fish onto which ultraviolet light has been radiated, and outputting the freshness information indicating freshness of the fish on the basis of the foregoing information. In the step of outputting, a result of a determination as to freshness is output. More specifically, identified freshness is output on the basis of data obtained from a result of an experiment, data obtained from theoretical rationalization based on an experiment, or the like. Since freshness is identified using the luminance of the iris portion of the eye of the fish obtained as a result of measurement (image capture or the like) of the luminance of the eye of the fish through radiation of ultraviolet light, the fish need not be filleted, and freshness information regarding a fish that is not so transparent can be output.

The information indicating luminance is an index indicating the brightness of an image in unit area. A luminance value may be, for example, a value (for example, in candela) obtained by measuring an obtained image using a luminance meter, or may be information in which the brightness of each pixel in image data is represented by 8-bit or 16-bit tones.

In the case of a color image, RGB tones may be used as luminance values, or values obtained by weighting RGB luminance values may be used as luminance values.

Although the brightness of each pixel represented by 8-bit tones is described as a luminance value in the following embodiments, the luminance value may be a tone represented by a different number of bits, or may be a value measured by a luminance meter.

Here, for example, the method for outputting freshness information may include the steps of capturing an ultraviolet image of the eye of the fish onto which the ultraviolet light has been radiated, and extracting a luminance value of the iris portion from the ultraviolet image, determining the freshness of the fish on the basis of the luminance value of the iris portion, and outputting the freshness information. As a result, using image capture means such as a camera, the freshness of the fish can be determined relatively easily in a short period of time without invading the fish.

In addition, in the step of extracting, a luminance value of a crystalline lens portion may be extracted from the ultraviolet image and the freshness of the fish may be determined on the basis of a freshness index, which is obtained by normalizing the luminance value of the iris portion using the luminance value of the crystalline lens portion. In addition, in the step of extracting, the freshness index may be a difference between the luminance value of the iris portion and the luminance value of the crystalline lens portion, a value obtained by dividing the difference by the luminance value of the crystalline lens portion, or a ratio of the luminance value of the iris portion to the luminance value of the crystalline lens portion. As a result, the freshness of the fish can be determined while suppressing the effect of individual differences of fish, differences in image capture conditions, and the like.

In addition, in the step of capturing, the ultraviolet image may be captured by radiating the ultraviolet light and an infrared image of the eye of the fish may be captured by radiating infrared light. In the step of extracting, the freshness of the fish may be determined in accordance with a freshness index, which is obtained by normalizing the luminance value of the iris portion extracted from the ultraviolet image using a luminance value of an iris portion extracted from the infrared image. In addition, in the step of extracting, the freshness index may be a difference between the luminance value of the iris portion extracted from the ultraviolet image and the luminance value of the iris portion extracted from the infrared image, a value obtained by dividing the difference by the luminance value of the iris portion extracted from the infrared image, or a ratio of the luminance value of the iris portion extracted from the ultraviolet image to the luminance value of the iris portion extracted from the infrared image. As a result, the freshness of the fish can be determined while suppressing the effect of individual differences of fish, differences in image capture conditions, and the like.

In addition, in the step of extracting, the freshness of the fish may be determined by referring to predetermined determination information, in which each of a plurality of different pieces of freshness information and each of a plurality of ranges of values of the freshness index are associated with each other. As a result, the determination information may be determined using a result of an experiment and the freshness of the fish can be appropriately determined.

In addition, the freshness information may be represented by time elapsed since a fish died. The determination information may be information in which a longer time elapsed since a fish died is associated with a range of larger values of the freshness index. As a result, the freshness of the fish can be appropriately determined.

In addition, the step of extracting may include the steps of (a) detecting an edge portion in the ultraviolet image, and (b) detecting a portion similar to a double-circle pattern from the detected edge portion. The double-circle pattern may include a first circle and a second circle having a radius larger than that of the first circle. A region inside the first circle may include the crystalline lens portion. A region between an arc of the first circle and an arc of the second circle may include the iris portion. As a result, the crystalline lens portion and the iris portion can be identified from the ultraviolet image.

In addition, a freshness information output apparatus in the present disclosure is a freshness information output apparatus including an obtainer that obtains information indicating luminance of an iris portion of an eye of a fish onto which ultraviolet light has been radiated, and an outputter that outputs freshness information indicating freshness of the fish determined on the basis of the foregoing information. Since the information indicating the luminance of the iris portion can be obtained in a short period of time without invading the fish, a user of this apparatus can promptly output the freshness information regarding the fish without spoiling the fish.

Here, for example, the freshness information output apparatus may include an ultraviolet light radiator that radiates the ultraviolet light, and a mobile information device. The mobile information device may include an image capturer that captures an image at a time when the ultraviolet radiator radiates the ultraviolet light and an outputter that determines the freshness of the fish on the basis of a luminance value of the iris portion extracted from the image captured by the image capturer and that displays information indicating a result of the determination. As a result, the user can learn the freshness of fish in various places using the mobile information device such as a smartphone.

It should be noted that general or specific embodiments may be implemented as a system, a method, an integrated circuit, a computer program, a storage medium, or any selective combination thereof.

Embodiments will be described hereinafter with reference to the drawings. The embodiments described herein are specific examples of the present disclosure. Therefore, values, shapes, materials, components, arrangement and connection modes of the components, steps (procedure), and order of the steps mentioned in the embodiments are examples and do not limit the present disclosure. Among the components mentioned in the embodiments, those not described in the independent claims, which define the broadest concepts of the present disclosure, are components that may be arbitrarily added. Each figure is a schematic diagram and is not necessarily a strict illustration.

In the embodiments, a freshness information output apparatus as an aspect that performs, by conducting an analysis of an ultraviolet image of an eye of a fish, a method for outputting freshness information in order to determine the freshness of the fish on the basis of the luminance of the eye of the fish will be mainly described.

First Embodiment

A freshness information output apparatus 100 according to a first embodiment of the present disclosure will be described with reference to the drawings as necessary.

Configuration

FIG. 1 is a functional block diagram illustrating the freshness information output apparatus 100 according to the first embodiment. As illustrated in FIG. 1, the freshness information output apparatus 100 includes an image capture unit 1 and a determination unit 2 as the functional components thereof. Here, the image capture unit 1 has a function of generating an image including an eye of a fish (sample) 9 by capturing an image of the fish 9. The determination unit 2 has a function of determining the freshness of the fish 9 on the basis of the image generated by the image capture unit 1 and outputting a result of the determination. The determination unit 2 includes an analysis section 3 that extracts image data corresponding to an iris and a crystalline lens of the eye of the fish 9 and a calculation section 4 that calculates a certain index (hereinafter referred to as a "freshness index A") from the image data. The determination unit 2 accumulates determination information 8 used for determining the freshness of fish in accordance with the freshness index A.

Figure 2:
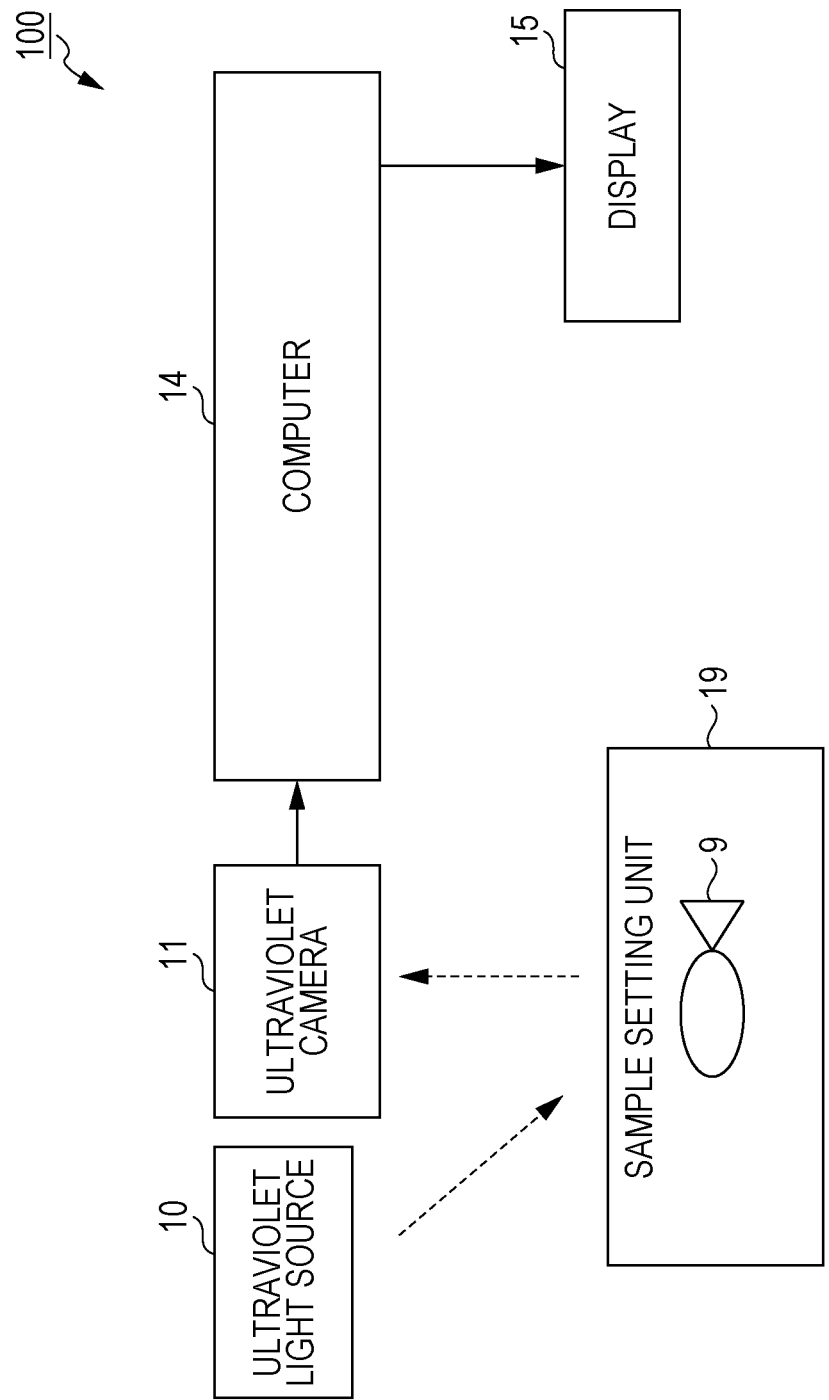
FIG. 2 is a diagram illustrating the hardware configuration of the freshness information output apparatus according to the first embodiment.

FIG. 2 is a diagram illustrating the hardware configuration of the freshness information output apparatus 100 according to the first embodiment. As illustrated in FIG. 2, the freshness information output apparatus 100 includes an ultraviolet light source 10, an ultraviolet camera 11, a sample setting unit 19, a computer 14, and a display 15. Here, the computer 14 includes a memory, a processor, an input device, and an interface for connecting a device and operates as a device for realizing the function of the determination unit 2 by executing a control program stored in the memory using the processor. The computer 14 may include, in addition to the memory (main storage device), an auxiliary storage device such as a hard disk device.

The function of the image capture unit 1 is realized by radiating ultraviolet rays (ultraviolet light) onto the fish 9 set on the sample setting unit 19 using the ultraviolet light source 10, receiving light reflected from the fish 9 using the ultraviolet camera 11, and generating an image including the eye of the fish 9. The sample setting unit 19 is a member (for example, a tray) on which the fish 9 can be stably set so that an image of the eye of the fish 9 can be captured.

The ultraviolet light source 10 is a light source capable of radiating light having a wavelength in an ultraviolet range (for example, a wavelength range of 300 to 400 nm). The ultraviolet camera 11 receives light having a wavelength in the ultraviolet range to capture an image.

The function of the determination unit 2 is realized by the computer 14 and the display 15. That is, the function of the determination unit 2 is realized when the computer 14 obtains, through the interface for connecting a device or the like, an image including the eye of the fish 9 captured by the ultraviolet camera 11, calculates the freshness index A by analyzing the image, determines the freshness of the fish 9 on the basis of the freshness index A, and displays information indicating a result on the display 15. The determination information 8 accumulated in the storage device of the computer 14, such as the memory, is used for determining the freshness of the fish 9. As processes for analyzing the image, the computer 14 performs a process for extracting a portion of the image including the eye of the fish 9, a process for distinguishing an iris portion and a crystalline lens portion of the eye of the fish 9, a process for calculating the average luminance values of the iris portion and the crystalline lens portion, a process for calculating the freshness index A on the basis of a difference between the luminance values, and the like.

Operations

Figure 3:
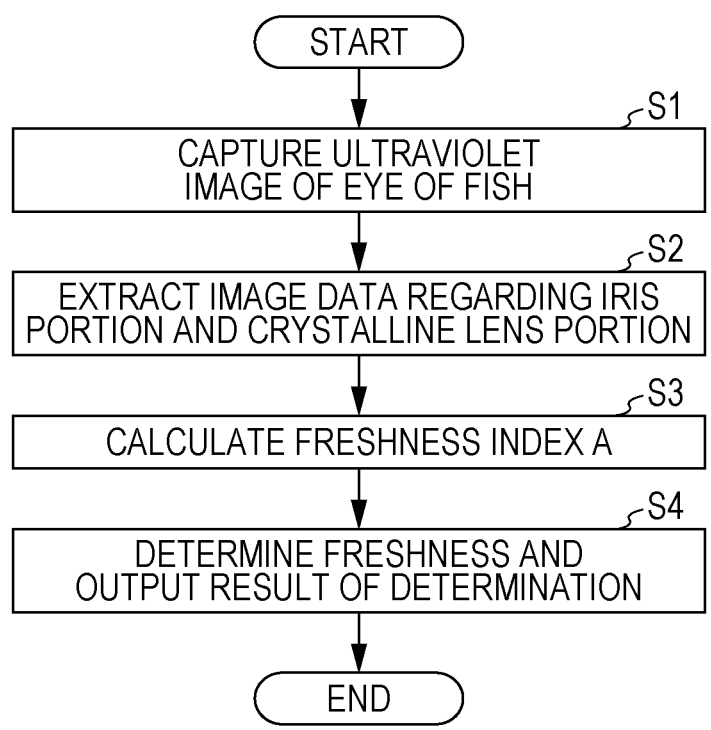
FIG. 3 is a flowchart illustrating operations performed by the freshness information output apparatus according to the first embodiment.

FIG. 3 is a flowchart illustrating operations performed by the freshness information output apparatus 100.

The operations performed by the freshness information output apparatus 100 having the above-described configuration will be described hereinafter in accordance with the flowchart of FIG. 3, while explaining individual steps with reference to FIGS. 4 to 9B.

With the fish 9 set on the sample setting unit 19, the image capture unit 1 generates an image (ultraviolet image) including the eye of the fish 9 by causing the ultraviolet light source 10 to radiate light and the ultraviolet camera 11 to capture the image (processing step S1). The generated image is a group of image data (luminance values) obtained at pixel positions included in a two-dimensional image space. The luminance values are represented by, for example, 8-bit data (256 tones). In order to improve the accuracy of determining the freshness of the fish 9, for example, it is somewhat effective to increase, by, for example, adjusting the direction of the optical axis and the angle of view of the ultraviolet camera 11, the size of an image to be generated, and the like, the resolution of the ultraviolet camera 11 in a portion corresponding to the entirety of the eye of the fish 9 and a surrounding area.

Next, the determination unit 2 obtains the image generated by the image capture unit 1 and extracts image data regarding the iris portion and the crystalline lens portion of the eye of the fish 9 from the image using the analysis section 3 (processing step S2). The extraction of the image data regarding the iris portion and the crystalline lens portion may be realized using any method, but, for example, the following method may be used.

Figure 4:
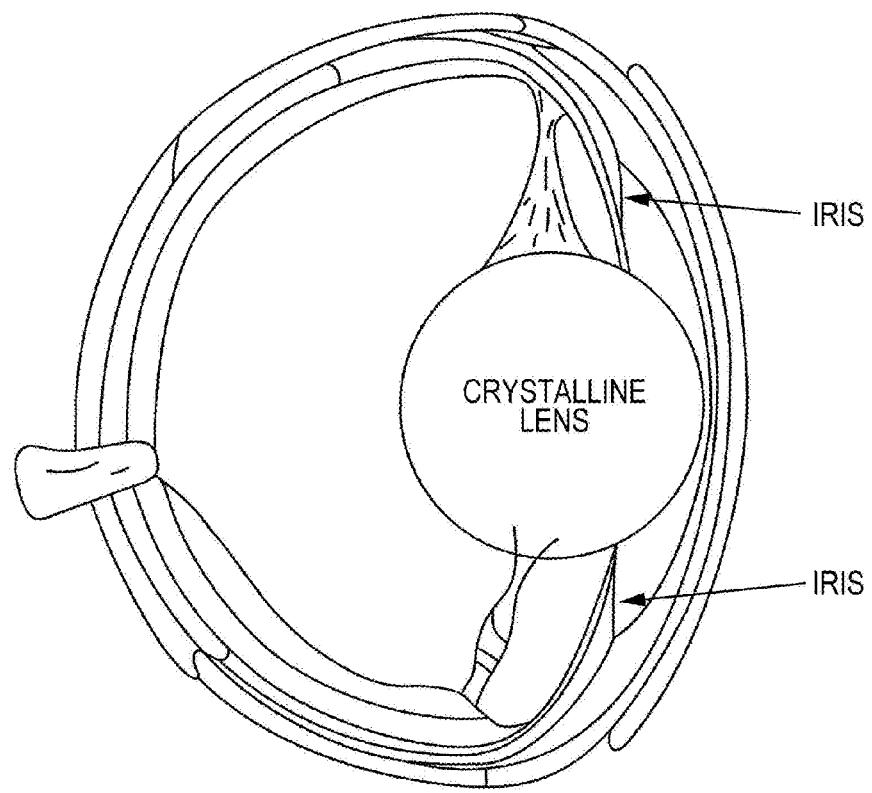
FIG. 4 is a sectional view indicating the positions of an iris and a crystalline lens of an eye of a fish.
Figure 5:
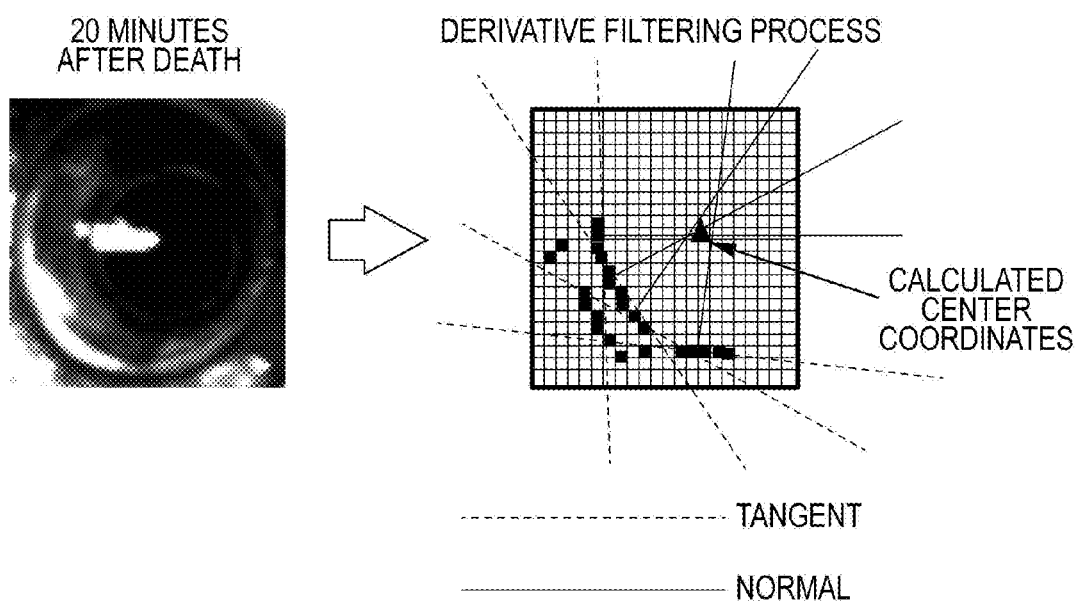
FIG. 5 is a diagram illustrating a method for calculating the center of an eye of a fish.

First, a first derivative filter is applied to the image including the eye of the fish 9 to obtain an image indicating portions in which spatial gradients of data values (luminance values) are steep (for example, larger than a certain threshold), that is, portions in which strong contrasts are observed (a so-called "edge portions"). Among these edge portions, a portion (a position corresponding to the double-circle pattern) that is the most similar to a double-circle pattern, which indicates a boundary between the eye of the fish 9 and the surrounding area and a boundary between the iris portion and the crystalline lens portion of the eye of the fish 9, is detected through pattern matching or the like. Next, at the detected position corresponding to the double-circle pattern, a portion of the captured image inside an inner circle of the double-circle pattern is identified as a crystalline lens portion, and a portion between the inner circle and an outer circle of the double-circle pattern is identified as an iris portion. As illustrated in FIG. 4, the iris surrounds the crystalline lens. The iris portion indicates the iris of the eye of the fish 9, and the crystalline lens portion indicates the crystalline lens of the eye of the fish 9.

If an arc can be identified from a boundary formed by edge portions obtained by applying the first derivative filter, the center of a circle may be calculated from the arc, and the pattern matching may be performed using concentric circles having the center in common as a candidate to be matched with the double-circle pattern. Now, a method for calculating the center of a circle from edge portions will be described with reference to FIG. 5. First, one or more broken curves obtained by connecting edge portions (portions in which spatial gradients of luminance are steep) obtained by applying the first derivative filter to an obtained image (an ultraviolet image showing a fish 20 minutes after its death in the example illustrated in FIG. 5) are calculated. Next, a tangent (each broken line illustrated in FIG. 5) is calculated for a point on each of the one or more curves, and a normal (each solid line illustrated in FIG. 5) through the point perpendicular to the tangent is calculated. This calculation of a normal is performed for each point, and a point at which the normals intersect is determined as the center of a circle (the center coordinates of an eye of a fish). Since, unlike a human eye, an eye of a fish does not have eyelashes or an eyelid, the center of an eye of a fish can be identified using this method. When the iris portion and the crystalline lens portion of an eye of a fish are distinguished using a double-circle pattern or the like, a difference in luminance between the iris portion and the crystalline lens portion (a difference between the average luminance values of these regions) larger than a certain value may be required on the basis of luminance distribution.

After the analysis section 3 extracts the image data regarding the iris portion and the crystalline lens portion of the eye of the fish 9, the calculation section 4 of the determination unit 2 calculates, on the basis of the average luminance values of the extracted iris portion and crystalline lens portion, the freshness index A for evaluating the freshness of the fish 9 (processing step S3). Here, the average luminance value of the iris portion is an average of the luminance values of pixels of the image included in the iris portion, and the average luminance value of the crystalline lens portion is an average of the luminance values of pixels of the image included in the crystalline lens portion. A portion used for calculating the average luminance value of the iris portion, however, need not be the entirety of the iris portion, but, for example, may be a portion obtained by removing a certain region around the boundary between the iris portion and the crystalline lens portion from the iris portion. Similarly, a portion used for calculating the average luminance value of the crystalline lens portion need not be the entirety of the crystalline lens portion, but, for example, may be a portion obtained by removing a certain region around a boundary between the iris portion and the crystalline lens portion from the crystalline lens portion.

For example, luminance values to be obtained may be those larger than a certain lower threshold but smaller than a certain upper threshold. A portion used for calculating the average luminance value of the crystalline lens portion need not be the entirety of the crystalline lens portion, but may be a portion obtained by removing, from the crystalline lens portion, portions in which luminance values are smaller than or equal to the certain lower threshold or equal to or larger than the certain upper threshold.

The freshness index A is obtained by normalizing the average luminance value of the iris portion using the average luminance value of the crystalline lens portion and, for example, is a value (a difference between the average luminance values of the iris portion and the crystalline lens portion) obtained by subtracting the average luminance value of the crystalline lens portion from the average luminance value of the iris portion. Alternatively, the freshness index A may be a value obtained by dividing the difference between the average luminance values of the iris portion and the crystalline lens portion by the average luminance value of the crystalline lens portion, or may be a ratio of the average luminance value of the iris portion to the average luminance value of the crystalline lens portion. Here, the luminance of the iris portion and the crystalline lens portion, which is used for calculating the freshness index A, will be described hereinafter with reference to FIGS. 6 to 8, which indicate results of an experiment conducted by the present inventors using a fish.

FIG. 6 illustrates images, captured by an ultraviolet camera, of an eye of a fish kept at room temperature (temperature of 20° C.) and a humidity of 100%. In FIG. 6, images captured 20 minutes, 4 hours, and 7 hours after the fish died are illustrated. As illustrated in FIG. 6, only the iris portion of the eye of the fish began to turn white 4 hours after the fish died.

FIG. 7 is a graph illustrating temporal changes in the luminance of the iris portion and the crystalline lens portion of the eye of the fish kept at room temperature (temperature of 20° C.) and a humidity of 100%. Changes in the luminance of the crystalline lens portion over time were small 6 hours or more after the fish died, whereas the luminance of the iris portion increased as time passed. As a result of another experiment conducted by the present inventors, it could be found that how the luminance of the iris portion increased over time could be different depending on the kind of fish. In addition, as a result of yet another experiment conducted by the present inventors, it could be found that, when the same kind of fish is used, the absolute value of luminance might be different between individuals, but how the iris portion turned white over time was similar between individuals.

FIG. 8 is a graph illustrating temporal changes in the difference between the average luminance values of the iris portion and the crystalline lens portion of each of a plurality of (four) fish kept at room temperature (temperature of 20° C.) and a humidity of 100%. The difference between the average luminance values increased over time in a similar manner even with different individuals. The difference between the average luminance values was obtained after the average luminance value of the iris portion was normalized using the average luminance value of the crystalline lens portion. As result of the normalization, the effect of individual differences between the fish can be removed to some extent. The effect of individual differences between the fish includes not only the brightness of the eyes of the fish but also differences in image capture conditions such as an image capture distance caused by individual differences such as the shapes and sizes of the fish. Thus, the freshness index A, which is obtained by normalizing the average luminance value of the iris portion using the average luminance value of the crystalline lens portion, could serve as an effective index correlated with the time elapsed since a fish died.

After the calculation section 4 calculates the freshness index A, the determination unit 2 determines the freshness of the fish 9 on the basis of the determination information 8 in accordance with the freshness index A and outputs information indicating a result of the determination (processing step S4). The determination information 8 is, for example, a mathematical expression or a table indicating, when freshness is represented by time elapsed since death, a correlation between the freshness index A and the time elapsed since death. In this case, the freshness of a fish is determined by referring to the determination information 8 and identifying the time elapsed since death in accordance with the freshness index A. The determination information 8 (for example, a mathematical expression or a table indicating a correlation between the freshness index A and the time elapsed since death) may be created in advance on the basis of the graph of FIG. 8 or results of an experiment.

FIG. 9A is a table, which is an example of the determination information 8 at a time when the difference between the average luminance values of the iris portion and the crystalline lens portion is used as the freshness index A, in which the ranges of values of the freshness index A and the time elapsed since death at room temperature are associated with each other. The table indicates a correspondence in which the time elapsed since death becomes longer as the freshness index A, which is the difference between the average luminance values, increases. That is, in this table, a longer time elapsed since a fish died is associated with a range of larger values of the freshness index A. According to this example, if the freshness index A calculated for a fish is, for example, smaller than or equal to 100 and it is assumed that the fish has been kept at room temperature, it can be determined that the time elapsed since the fish died is "shorter than 6 hours", which means the fish is relatively fresh. If the calculated freshness index A is, for example, 140, 150, or the like, the determination unit 2 determines that the time elapsed since the fish died is "12 hours or longer but shorter than 18 hours", which means that the fish is not so fresh. If the value obtained by dividing the difference between the average luminance values of the iris portion and the crystalline lens portion by the average luminance value of the crystalline lens portion or the ratio of the average luminance value of the iris portion to the average luminance value of the crystalline lens portion is used as the freshness index A, a table corresponding to the value or the ratio may be created and used for determinations.

Although the time elapsed since death illustrated in FIG. 9A is used as the freshness information in this embodiment, information indicating the degree of freshness such as, as illustrated in FIG. 9B, "very fresh (edible raw)", "fresh (inedible raw)", "still fresh (inedible raw)", and "not fresh (inedible)" may be used as the freshness information, instead.

In order to appropriately determine freshness after capturing an image of a fish, the determination information 8 is desirably realized as a table that suits the kind of fish and preservation conditions (temperature, humidity, and the like). For example, values of the freshness index A according to the elapsed time may be measured in advance for various kinds of fish under various preservation conditions, and a plurality of tables may be created for various kinds of fish under various preservation conditions and stored in the memory of the computer 14 or the like. An appropriate table may then be selected and used in accordance with the kind of fish whose image is to be captured and the preservation conditions. In this case, a user of the freshness information output apparatus 100 may input the kind of fish whose image is to be captured and the preservation conditions to the computer 14 through the input device before capturing an image of the fish, and the determination unit 2 may select a table in accordance with the information input by the user. Thus, by creating tables for various kinds of fish, freshness can be determined regardless of the transparency of a body of a fish whose image is to be captured.

The determination unit 2 outputs information indicating a result of a determination by, for example, displaying information indicating the time elapsed since a fish died, such as "12 hours or longer but shorter than 18 hours", on the display 15. As a result, the user of the freshness information output apparatus 100 can learn the freshness of the fish.

Thus, the freshness information output apparatus 100 captures an image of an eye of a fish and a surrounding area using the ultraviolet camera 11 and determines the freshness of the fish on the basis of the average luminance value of the iris portion of the eye of the fish or the like using the computer 14. Accordingly, the freshness of the fish can be determined in a short period of time without invading the fish.

The analysis section 3 detects, in an obtained image including an eye of a fish, the boundary between the iris portion and the crystalline lens portion by, for example, applying the first derivative filter in this embodiment. If the time elapsed since the fish died is short, however, it might be difficult to detect the boundary using the first derivative filter. For example, as illustrated in FIG. 10A, if the first derivative filter is applied (steep spatial gradients of luminance are extracted) to an image showing a fish 7 hours after its death, the iris portion and the crystalline lens portion can be distinguished by determining extracted edge portions as a boundary. On the other hand, as illustrated in FIG. 10B, if the first derivative filter is applied to an image showing a fish 20 minutes after its death, extracted edge portions only form a short arc, not a circle. In this case, if the arc is extremely short, the accuracy of calculating the center of a circle becomes extremely low, thereby making it difficult to distinguish the iris portion and the crystalline lens portion. Therefore, if the length of an obtained arc is shorter than a certain threshold (for example, if the obtained arc is shorter than a quarter of the circumference of a circle having the center obtained using the method described with reference to FIG. 5), it is difficult to detect the boundary between the iris portion and the crystalline lens portion, and accordingly the freshness index A may be automatically determined as a certain value. If the freshness index A is automatically determined as a certain value, the calculation of the freshness index A performed by the calculation section 4 is omitted, and the determination unit 2 determines freshness on the basis of the determined freshness index A. For example, if the difference between the average luminance values of the iris portion and the crystalline lens portion is used as the freshness index A and it is difficult to detect the boundary between the iris portion and the crystalline lens portion, the freshness index A may be automatically determined (regarded) as 0 (or a certain value close to 0). If the value obtained by dividing the difference between the average luminance values of the iris portion and the crystalline lens portion by the average luminance value of the crystalline lens portion is used as the freshness index A and it is difficult to detect the boundary between the ids portion and the crystalline lens portion, the freshness index A may be automatically determined (regarded) as 0 (or a certain value close to 0). If the ratio of the average luminance value of the iris portion to the average luminance value of the crystalline lens portion is used as the freshness index A and it is difficult to detect the boundary between the iris portion and the crystalline lens portion, the freshness index A may be automatically determined (regarded) as 1 (or a certain value close to 1).

Example

An example in which the freshness information output apparatus 100 is included in a portable smartphone (mobile information device) 101 will be described hereinafter.

Figure 11A:
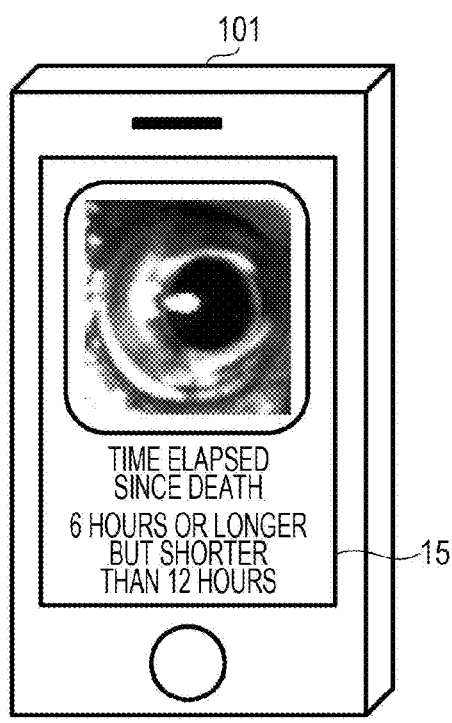
FIGS. 11A and 11B are images of a smartphone including the freshness information output apparatus.
Figure 11B:
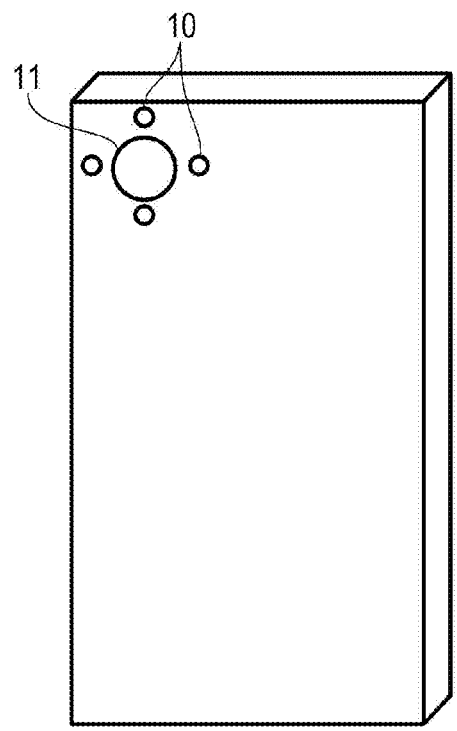

FIGS. 11A and 11B are images of the smartphone 101 including the freshness information output apparatus 100. The smartphone 101 illustrated in FIGS. 11A and 11B includes the computer 14. The display 15 illustrated in FIG. 11A is a liquid crystal display (or, for example, an organic electroluminescent (EL) display) mounted on a surface of a case of the smartphone 101. The ultraviolet camera 11 illustrated in FIG. 11B is a camera mounted on the case of the smartphone 101, and the ultraviolet light sources 10 are ultraviolet light-emitting diodes (LEDs) mounted around the ultraviolet camera 11. The smartphone 101 is used close to the eye of the fish 9. The smartphone 101 radiates ultraviolet rays to the eye of the fish 9 from the ultraviolet LEDs, receives reflected light using the camera (image sensor), and generates an image (ultraviolet image). The computer 14, which serves as the memory and the processor of the smartphone 101 and the like, functions as the determination unit 2 including the analysis section 3 and the calculation section 4 to determine the freshness (the time elapsed since death or the like) of the fish 9 on the basis of an image including the eye of the fish 9 and display information indicating a result of the determination on the liquid crystal display. The smartphone 101 is configured to also display the generated image on the liquid crystal display. As a result, a user can confirm that an image of the eye of the fish 9 has been captured and learn the freshness of the fish 9.

Figure 12:
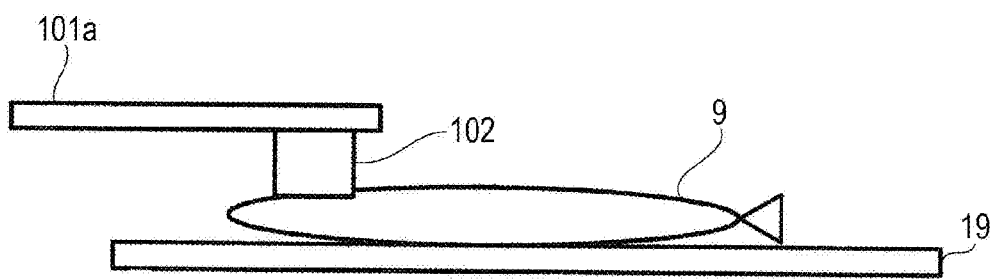
FIG. 12 is a diagram illustrating a method for capturing an image of an eye of a fish using a smartphone and an adapter.
Figure 13:
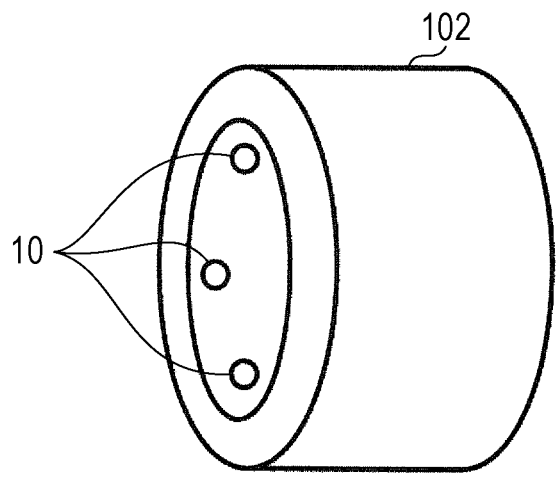
FIG. 13 is a schematic diagram illustrating the adapter mounted on the smartphone.
Figure 14:
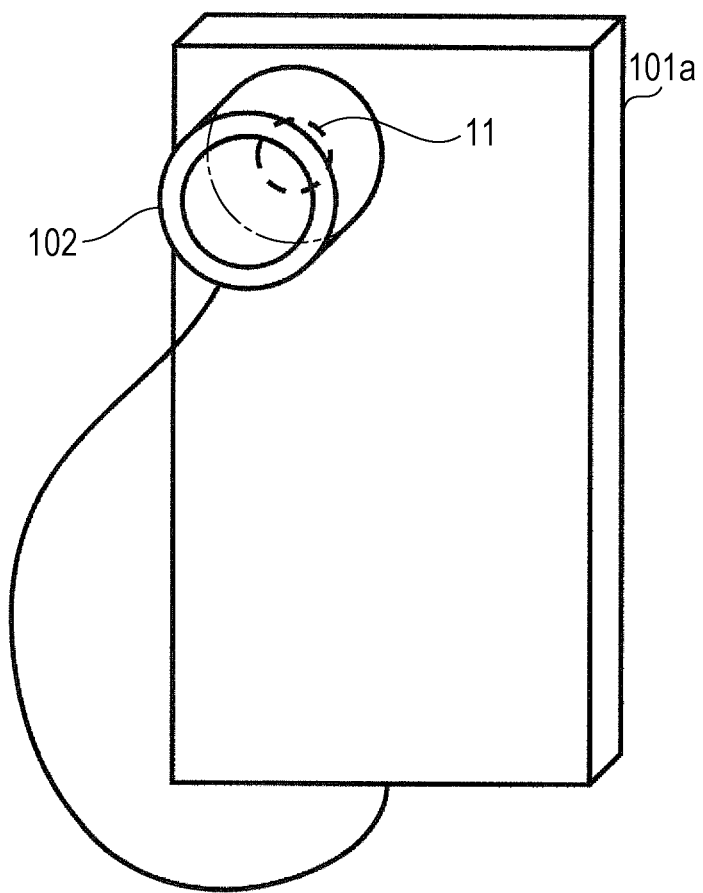
FIG. 14 is an image the smartphone and the adapter connected to each other.

As illustrated in FIG. 12, an adapter 102 including ultraviolet LEDs for radiating ultraviolet light onto an eye of a fish may be mounted on a smartphone 101a, which is configured by removing the ultraviolet LEDs from the smartphone 101, and a camera of the smartphone 101a may capture an image of the eye of the fish 9. In this case, the adapter 102 functions as an ultraviolet radiation unit (a component for radiating ultraviolet light), which is part of the function of the image capture unit 1 of the freshness information output apparatus 100 included in the smartphone 101a. FIG. 13 is a schematic diagram illustrating the adapter 102 mounted on the smartphone 101a. As illustrated in FIG. 13, the adapter 102 has a tubular shape and includes ultraviolet LEDs as the ultraviolet light source 10 in an inner wall thereof. In addition, as illustrated in FIG. 14, the adapter 102 is connected to an external interface unit of the smartphone 101a, and the smartphone 101a supplies a control signal and power to the adapter 102 through the external interface unit. The image sensor of the camera of the smartphone 101a may be one capable of receiving light having wavelengths of 300 to 800 nm, which is generally used as a camera of a smartphone. If the ultraviolet LEDs of the adapter 102 radiate near-ultraviolet rays within a range of wavelengths of 300 to 400 nm, an ultraviolet image can be appropriately captured. The smartphone 101a supplies a control signal to the adapter 102 in accordance with a user operation performed on the smartphone 101a, and the adapter 102 radiates ultraviolet light in accordance with the control signal. The smartphone 101a captures an image using the camera and displays the image of a fish and information indicating the freshness of the fish on the liquid crystal display.

Figure 15:
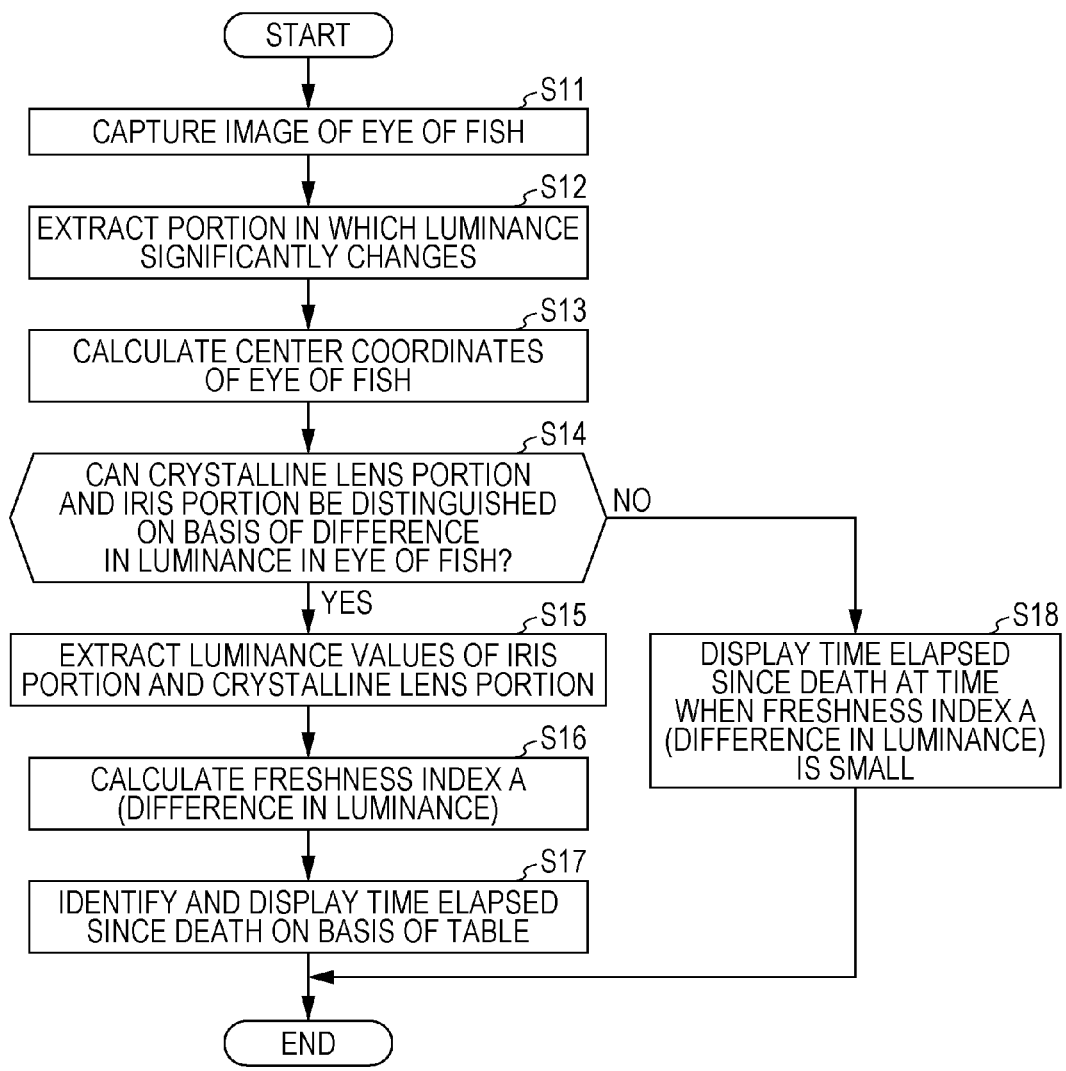
FIG. 15 is a flowchart illustrating an example of operations performed by the smartphone.

FIG. 15 is a flowchart illustrating an example of operations performed by the smartphone 101a including the freshness information output apparatus 100 and the adapter 102. If a user performs an operation for activating an application (program) for outputting freshness information regarding a fish using the smartphone 101a, the operations illustrated in FIG. 15 start.

If the user sets the adapter 102 on an eye of a fish and performs an operation for capturing an image of the eye of the fish using the camera of the smartphone 101a, the smartphone 101a issues a control signal for radiating ultraviolet rays from the ultraviolet LEDs of the adapter 102, and the camera captures an image (processing step S11).

Next, the smartphone 101a extracts portions (so-called "edge portions", where spatial gradients of luminance are steep) of the captured image in which luminance significantly changes (processing step S12) and calculates the center coordinates of the eye of the fish from the extracted edge portions (processing step S13).

Next, the smartphone 101a determines whether the iris portion and the crystalline lens portion can be distinguished in the eye of the fish in the image (processing step S14). If the iris portion and the crystalline lens portion can be distinguished, the smartphone 101a extracts the luminance values of the iris portion and the crystalline lens portion (processing step S15). The eye of the fish in the image is obtained through pattern matching or the like in which a double-circle pattern (luminance pattern) prepared for finding the eye of the fish on the basis of the extracted center coordinates is used. If changes in luminance in a region from the iris portion to the crystalline lens portion are sufficiently large, that is, for example, if the eye of the fish matches the double-circle pattern, and accordingly the boundary between the iris portion and the crystalline lens portion can be identified, the iris portion and the crystalline lens portion can be distinguished. The freshness index A, which is the difference between the extracted luminance values of the iris portion and the crystalline lens portion, is then calculated (processing step S16), and the time elapsed since the fish died is identified on the basis of the table (refer to FIGS. 9A and 9B), which is the determination information 8, and displayed as information indicating the freshness of the fish (processing step S17).

If the iris portion and the crystalline lens portion cannot be distinguished in processing step S14, information in the table (refer to FIGS. 9A and 9B) indicating that the time elapsed since the fish died is short is displayed (processing step S18). If the iris portion and the crystalline lens portion cannot be distinguished, the freshness index A may be regarded as 0, and the time elapsed since death according to the freshness index A may be obtained from the table and displayed.

Thus, by capturing an image of an eye of a fish using the smartphone 101a, the user can learn the freshness of the fish (the time elapsed since death) by seeing the liquid crystal display of the smartphone 101a.

Second Embodiment

A freshness information output apparatus 200 according to a second embodiment of the present disclosure will be described hereinafter with reference to the drawings. The freshness information output apparatus 200 is obtained by changing part of the freshness information output apparatus 100 according to the first embodiment. Description of the same components as those of the freshness information output apparatus 100 is omitted as necessary.

Configuration

Figure 16:
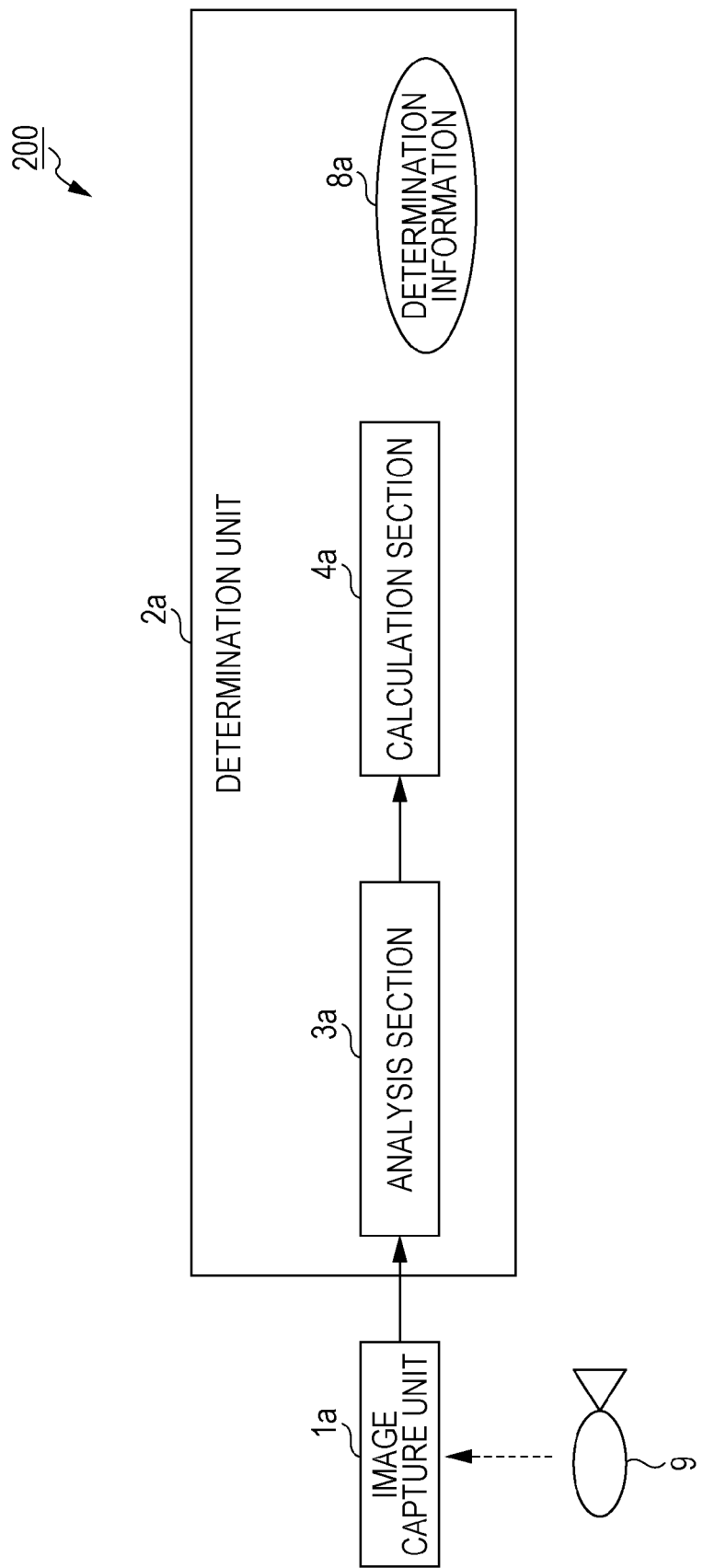
FIG. 16 is a functional block diagram illustrating a freshness information output apparatus according to a second embodiment.

FIG. 16 is a functional block diagram illustrating the freshness information output apparatus 200 according to the second embodiment. As illustrated in FIG. 16, the freshness information output apparatus 200 includes an image capture unit 1a and a determination unit 2a as the functional components thereof. Here, as with the image capture unit 1 according to the first embodiment, the image capture unit 1a has a function of capturing an image of a fish (sample) and generating an image including an eye of the fish, but unlike the image capture unit 1, the image capture unit 1a generates an infrared image as well as an ultraviolet image. The determination unit 2a has a function of determining the freshness of the fish on the basis of the ultraviolet image and the infrared image generated by the image capture unit 1a and outputting a result of the determination. The determination unit 2a includes an analysis section 3a that extracts image data corresponding to the ids portion of the eye of the fish from each of the ultraviolet image and the infrared image and a calculation section 4a that calculates a certain index (hereinafter referred to as a "freshness index B") from the image data. The determination unit 2a accumulates determination information 8a for determining the freshness of the fish in accordance with the freshness index B.

Figure 17:
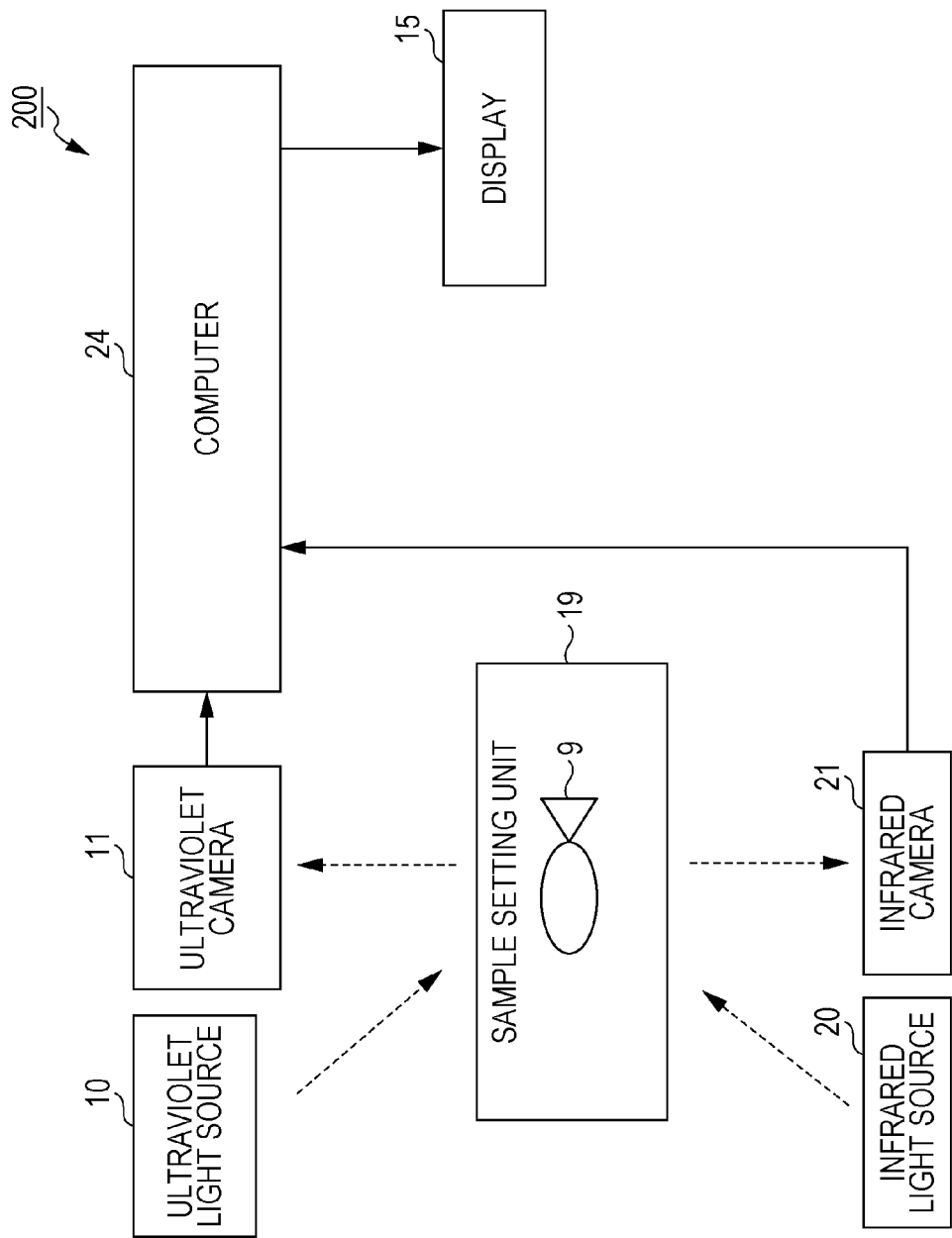
FIG. 17 is a diagram illustrating the hardware configuration of the freshness information output apparatus according to the second embodiment.

FIG. 17 is a diagram illustrating the hardware configuration of the freshness information output apparatus 200 according to the second embodiment. As illustrated in FIG. 17, the freshness information output apparatus 200 includes the ultraviolet light source 10, the ultraviolet camera 11, the display 15, and the sample setting unit 19, which are the same as those included in the freshness information output apparatus 100 according to the first embodiment. The freshness information output apparatus 200 also includes a computer 24, which is obtained by changing part of the function of the computer 14 according to the first embodiment, an infrared light source 20, and an infrared camera 21. As with the computer 14, the computer 24 includes a memory, a processor, an input device, and an interface for connecting an interface and operates as a device for realizing the function of the determination unit 2a by executing a control program, which is different from the control program according to the first embodiment, stored in the memory using the processor.

The function of the image capture unit 1a is realized by capturing images of a fish set on the sample setting unit 19 and generating an ultraviolet image and an infrared image including an eye of the fish using the ultraviolet camera 11 and the infrared camera 21. The ultraviolet image is generated by radiating ultraviolet rays onto the fish from the ultraviolet light source 10 and receiving light reflected from the fish using the ultraviolet camera 11. The infrared image is generated by radiating infrared rays (infrared light) onto the fish from the infrared light source 20 and receiving light reflected from the fish using the infrared camera 21.

The infrared light source 20 is a light source that radiates light having a wavelength in an infrared range (for example, a wavelength range of 700 to 1,000 nm), and the infrared camera 21 captures an image by receiving light having a wavelength in the infrared range.

The function of the determination unit 2a is realized by the computer 24 and the display 15. That is, the function of the determination unit 2a is realized by obtaining images including the eye of the fish captured by the ultraviolet camera 11 and the infrared camera 21 through the interface for connecting a device or the like, analyzing the images to calculate the freshness index B, determining the freshness of the fish on the basis of a result of the calculation, and displaying a result of the determination on the display 15. The determination information 8a accumulated in a storage device of the computer 24, such as the memory, is used for determining the freshness of the fish.

Operations

Operations performed by the freshness information output apparatus 200 having the above-described configuration will be described hereinafter in accordance with a flowchart of FIG. 18, while explaining individual steps with reference to FIGS. 19 to 22B.

Figure 18:
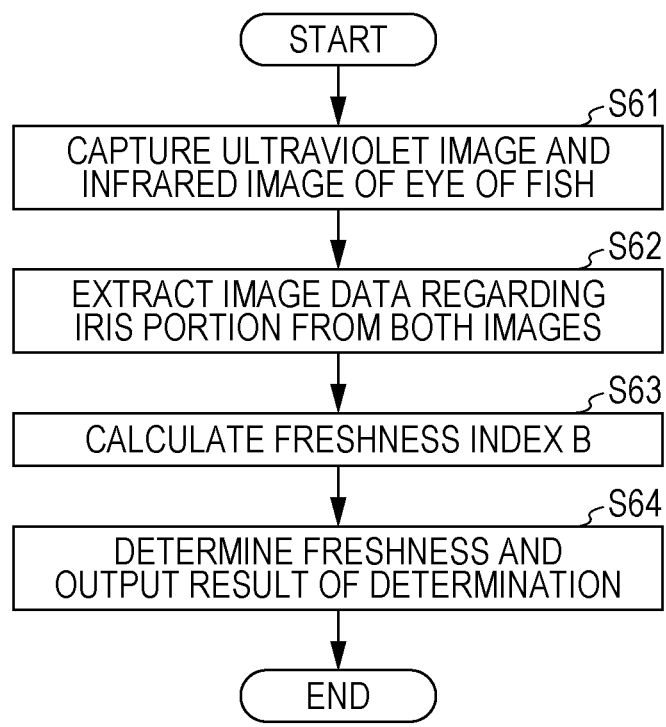
FIG. 18 is a flowchart illustrating operations performed by the freshness information output apparatus according to the second embodiment.

FIG. 18 is a flowchart illustrating the operations performed by the freshness information output apparatus 200.

The image capture unit 1a generates an ultraviolet image including an eye of a fish by causing the ultraviolet light source 10 to radiate ultraviolet rays and the ultraviolet camera 11 to capture an image of the fish and an infrared image including the eye of the fish by causing the infrared light source 20 to radiate infrared rays and the infrared camera 21 to capture an image of the fish (processing step S61). The generated ultraviolet image and infrared image are each a group of image data (luminance values) obtained at pixel positions included in a two-dimensional image space. The luminance values are represented by, for example, 8-bit data (256 tones). In order to improve the accuracy of determining the freshness of the fish, for example, it is somewhat effective to increase, by, for example, adjusting the direction of the optical axis and the angle of view of each of the ultraviolet camera 11 and the infrared camera 21, the sizes of images to be generated, and the like, the resolution of the ultraviolet camera 11 and the infrared camera 21 in a portion corresponding to the entirety of the eye of the fish and a surrounding area.

Next, the determination unit 2a obtains the ultraviolet image and the infrared image generated by the image capture unit 1a and extracts image data regarding the iris portion of the eye of the fish from these images (processing step S62). The extraction of the image data regarding the iris portion may be realized using any method, but, for example, the method described in the first embodiment may be used.

After the analysis section 3a extracts the image data regarding the iris portion of the eye of the fish from the ultraviolet image and the infrared image, the calculation section 4a calculates the freshness index B for evaluating the freshness of the fish on the basis of the average luminance values of the iris portion extracted from both images (processing step S63). Here, the average luminance value of the iris portion is an average of the luminance values of pixels of the image included in the iris portion. The freshness index B is obtained by normalizing the average luminance value of the iris portion of the ultraviolet image using the average luminance value of the iris portion of the infrared image and, for example, is a value (a difference between the average luminance values of the iris portions) obtained by subtracting the average luminance value of the iris portion of the infrared image from the average luminance value of the iris portion of the ultraviolet image. Alternatively, the freshness index B may be a value obtained by dividing the difference between the average luminance values of the iris portions of the ultraviolet image and the infrared image by the average luminance value of the iris portion of the infrared image, or may be a ratio of the average luminance value of the iris portion of the ultraviolet image to the average luminance value of the iris portion of the infrared image. Here, the luminance of the iris portions of the ultraviolet image and the infrared image, which is used for calculating the freshness index B, will be described hereinafter with reference to FIGS. 19 to 21, which indicate results of an experiment on a fish.

Figure 19:
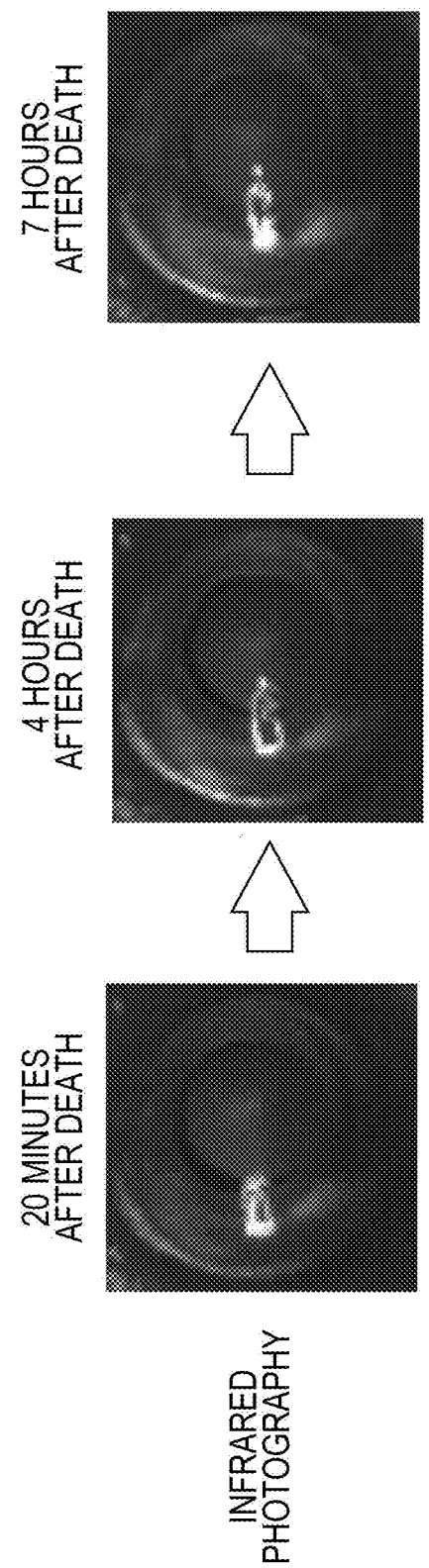
FIG. 19 is a diagram illustrating images of an eye of a fish captured by an infrared camera.

FIG. 19 illustrates images, captured by an infrared camera, of an eye of a fish kept at room temperature (temperature of 20° C.) and a humidity of 100%. In FIG. 19, images captured 20 minutes, 4 hours, and 7 hours after the fish died are illustrated. Although the iris portion of the eye of the fish began to turn white 4 hours after the fish died in the ultraviolet images illustrated in FIG. 6, no significant change in luminance over time is observed in the iris portion or other portions of the eye of the fish in the infrared images illustrated in FIG. 19.

Figure 20:
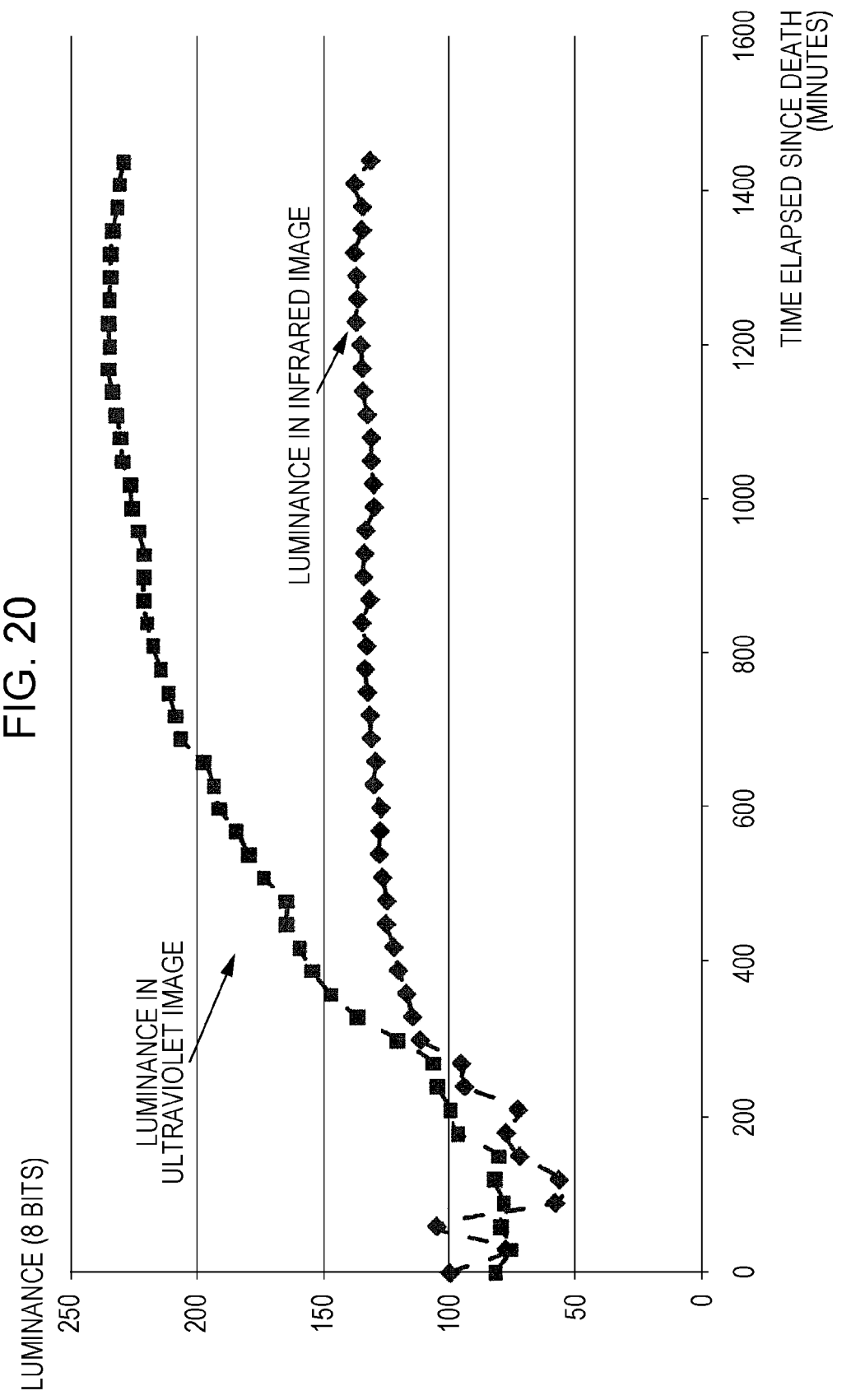
FIG. 20 is a graph illustrating temporal changes in the luminance of iris portions of an ultraviolet image and an infrared image.

FIG. 20 is a graph illustrating temporal changes in the luminance of the iris portion of the eye of the fish kept at room temperature (temperature of 20° C.) and a humidity of 100% in the ultraviolet image and the infrared image. As illustrated in FIG. 20, changes in the luminance of the iris portion of the infrared image over time were small, whereas the luminance of the iris portion of the ultraviolet image significantly changed as time passed.

Figure 21:
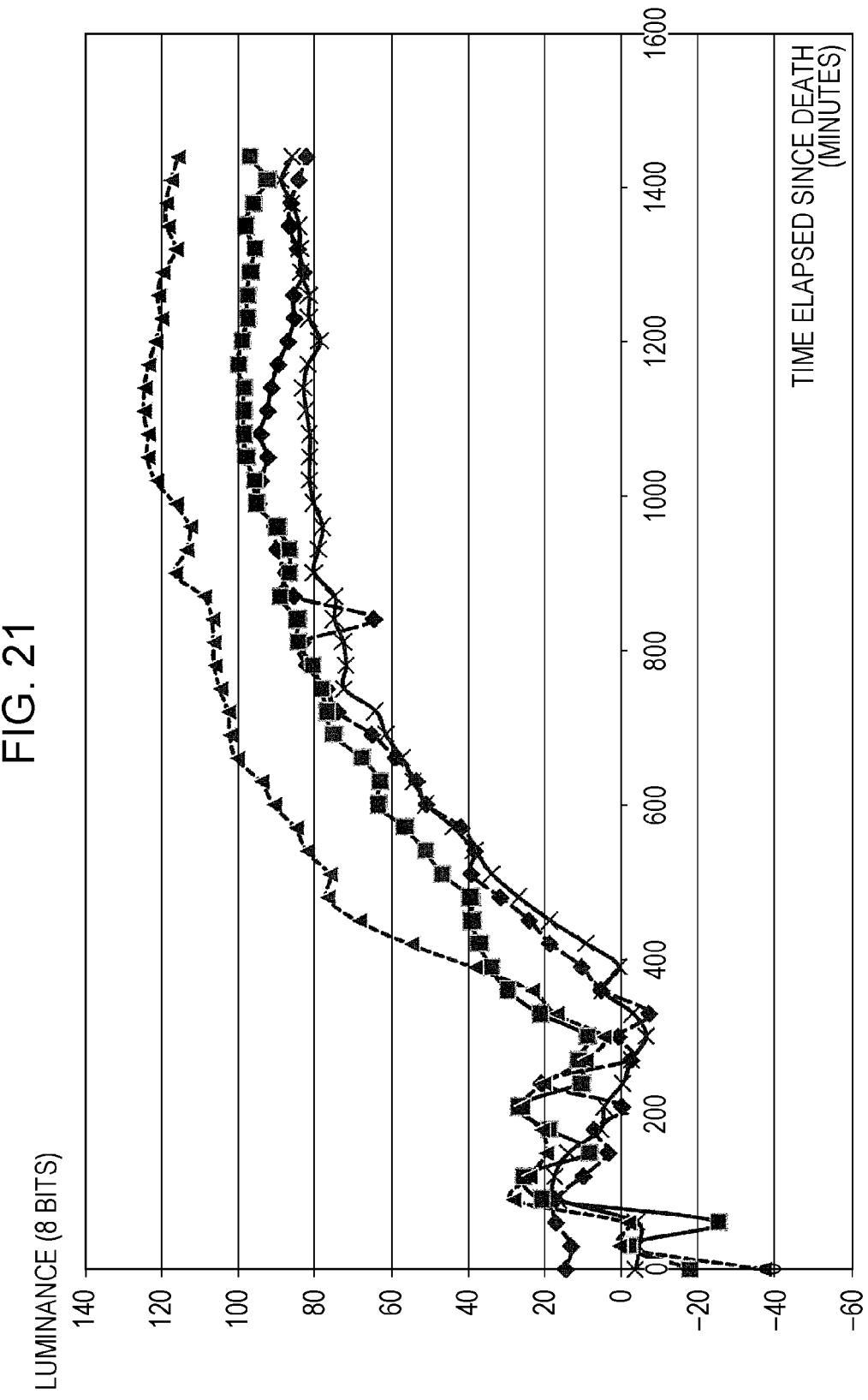
FIG. 21 is a graph illustrating temporal changes in a difference between the average luminance values of the iris portion of each of a plurality of fish in the ultraviolet image and the infrared image.

FIG. 21 is a graph illustrating temporal changes in the difference between the average luminance values of the iris portion of each of a plurality of (four) fish kept at room temperature (temperature of 20° C.) and a humidity of 100% in the ultraviolet image and the infrared image. The difference between the average luminance values of the two images increased over time in a similar manner even with different individuals. The difference between the average luminance values of the two images was obtained after the average luminance value of the iris portion of the ultraviolet image was normalized using the average luminance value of the iris portion of the infrared image. As a result of the normalization, the effect of individual differences between the fish that would have otherwise appeared on the images could be removed to some extent. The effect of individual differences between the fish includes not only the brightness of the eyes of the fish but also differences in image capture conditions such as an image capture distance caused by individual differences such as the shapes and sizes of the fish. Thus, the freshness index B, which is obtained by normalizing the average luminance value of the iris portion of the ultraviolet image using the average luminance value of the iris portion of the infrared image, can serve as an effective index correlated with the time elapsed since a fish died.

After the calculation section 4a calculates the freshness index B, the determination unit 2a determines the freshness of the fish on the basis of the determination information 8a in accordance with the freshness index B and outputs information indicating a result of the determination (processing step S64). The determination information 8a is, for example, a mathematical expression or a table indicating, when freshness is represented by time elapsed since death, a correlation between the freshness index B and the time elapsed since death. In this case, the freshness of a fish is determined by referring to the determination information 8a and identifying the time elapsed since death in accordance with the freshness index B. The determination information 8a (for example, a mathematical expression or a table indicating a correlation between the freshness index B and the time elapsed since death) may be created in advance on the basis of results of an experiment.

FIG. 22A is a table, which is an example of the determination information 8a at a time when the difference between the average luminance value of the iris portion of the ultraviolet image and the average luminance value of the iris portion of the infrared image is used as the freshness index B, in which the ranges of values of the freshness index B and the time elapsed since death at room temperature are associated with each other. The table indicates a correspondence in which the time elapsed since death becomes longer as the freshness index B, which is the difference between the average luminance values, increases. That is, in this table, a longer time elapsed since a fish died is associated with a range of larger values of the freshness index B. According to this example, if the freshness index B calculated for a fish is, for example, smaller than or equal to 30 and it is assumed that the fish has been kept at room temperature, it can be determined that the time elapsed since the fish died is "shorter than 8 hours", which means the fish is relatively fresh. If the calculated freshness index B is, for example, 90, 100, or the like, the determination unit 2a determines that the time elapsed since the fish died is "14 hours or longer but shorter than 24 hours", which means that the fish is not so fresh. If the value obtained by dividing the difference between the average luminance values of the iris portions of the ultraviolet image and the infrared image by the average luminance value of the iris portion of the infrared image or the ratio of the average luminance value of the iris portion of the ultraviolet image to the average luminance value of the ids portion of the infrared image is used as the freshness index B, a table corresponding to the value or the ratio may be created and used for determinations. In addition, as in the first embodiment, in order to appropriately determine freshness after capturing images of a fish, the determination information 8a is desirably realized as a table that suits the kind of fish and preservation conditions (temperature, humidity, and the like). For example, values of the freshness index B according to the elapsed time may be measured in advance for various kinds of fish under various preservation conditions, and a plurality of tables may be created for various kinds of fish under various preservation conditions and stored in the memory of the computer 24 or the like. An appropriate table may then be selected and used in accordance with the kind of fish whose image is to be captured and the preservation conditions. In this case, a user of the freshness information output apparatus 200 may input the kind of fish whose image is to be captured and the preservation conditions to the computer 24 through the input device before capturing images of the fish, and the determination unit 2a may select a table in accordance with the information input by the user.

The determination unit 2a outputs information indicating a result of a determination by, for example, displaying information indicating the time elapsed since a fish died, such as "14 hours or longer but shorter than 24 hours", on the display 15. As a result, the user of the freshness information output apparatus 200 can learn the freshness of the fish.

Although the analysis section 3a extracts image data regarding the iris portion from the obtained ultraviolet image and infrared image including an eye of a fish, it might be difficult to distinguish the iris portion from the eye of the fish. Therefore, image data regarding the entirety of the eye of the fish including the iris portion may be extracted. In this case, the calculation section 4a may calculate the freshness index B while regarding the average luminance value of the entirety of the eye of the fish in the ultraviolet image as the average luminance of the iris portion and the average luminance value of the entirety of the eye of the fish in the infrared image as the average luminance value of the iris portion. Here, the average luminance value of the entirety of the eye of the fish in each image is an average of luminance values obtained at pixels of each image included in the eye of the fish.

Thus, the freshness information output apparatus 200 captures an ultraviolet image and an infrared image of an eye of a fish using the ultraviolet camera 11 and the infrared camera 21 and determines the freshness of the fish on the basis of the average luminance value of the iris portion of each image or the like using the computer 24. Accordingly, the freshness of the fish can be determined in a short period of time without invading the fish.

Although the time elapsed since death illustrated in FIG. 22A is used as the freshness information in this embodiment, information indicating the degree of freshness such as, as illustrated in FIG. 22B, "very fresh (edible raw)", "fresh (inedible raw)", "still fresh (inedible raw)", and "not fresh (inedible)" may be used as the freshness information, instead.

Other Embodiments

Although the freshness information output apparatus according to each embodiment has been described, each embodiment is just an example and may be modified in various ways.

For example, when an image of an eye of a fish is captured in the first or second embodiment, a polarizing filter may be used to reduce distortion in the captured image due to halation or the like.

In addition, although the average luminance values of the iris portion and the crystalline lens portion are used for calculating the freshness index in the first and second embodiments, exact averages need not necessarily be used. A luminance value indicating the luminance of the iris portion and a luminance value indicating the luminance of the crystalline lens portion may be used for calculating the freshness index, instead.

In addition, although the freshness index A, which is obtained by normalizing the luminance value of the iris portion of an eye of a fish, is calculated and the time elapsed since death is determined in accordance with a result of the calculation on the basis of a table in which a longer time elapsed since a fish died is associated with a range of larger values of the freshness index A in the first embodiment, the normalization may be omitted. That is, the time elapsed since death may be determined in accordance with a luminance value of the iris portion of the eye of the fish obtained from an ultraviolet image on the basis of a table in which a larger luminance value of the iris portion is associated with a longer time elapsed since a fish died, instead.

In addition, although information indicating a result of a determination as to the freshness of a fish is output by displaying the information on the display 15 in the first and second embodiments, the information may be displayed on a screen projected by a projector, instead of the display 15. Alternatively, the output of the information indicating a result of the determination as to the freshness of a fish may be realized by means other than displaying the information, such as printing the information, emitting a sound indicating the information, or transmitting the information to another device.

In addition, although the freshness of a fish is represented by the time elapsed since death in the first and second embodiments, the elapsed time may be input and the freshness of a fish may be represented by the preservation conditions. For example, the preservation conditions (for example, temperature) may be determined on the basis of the plurality of tables for various kinds of fish under various preservation conditions, the input elapsed time, and the calculated freshness index (the freshness index A or B). Alternatively, the freshness of a fish may be represented as the degree of freshness such as "very fresh", "fresh", "not so fresh", or "bad", or may be represented as a value. That is, the freshness of a fish may be determined by identifying an item indicating freshness in accordance with the freshness index calculated from an image of an eye of the fish using determination information in which a plurality of items (values, character strings, images, or other type of information) indicating different degrees of freshness are associated with a plurality of ranges of values of the freshness index.

In addition, as with the freshness information output apparatus 100 according to the first embodiment, the freshness information output apparatus 200 according to the second embodiment may be applied to a smartphone. In this case, not only the ultraviolet light source 10 but also the infrared light source 20 (infrared LEDs as the infrared light source 20) may be removed from the image capture unit 1a and mounted on an adapter. In order to capture an ultraviolet image and an infrared image, the LEDs may be sequentially caused to radiate rays by controlling the smartphone.

In addition, the entirety or part of each of the above-described processes (the process illustrated in FIGS. 3, 15, and 18 and the like) may be performed only by the mechanisms and circuits (hardware) of one of various devices or may be performed by software. When software is used, each process is realized by executing a control program stored in a memory using a processor included in the device. Alternatively, the control program may be stored in a recording medium and distributed or sold in the market. For example, a device can perform each of the processes (the processes illustrated in FIGS. 3, 15, and 18 and the like) by installing the distributed control program thereon and causing a processor thereof to execute the distributed control program.

In addition, although an example in which the freshness information output apparatus 100 and the freshness information output apparatus 200 are each mainly configured by the single computer 14 (computer 24) has been described, the freshness information output apparatus may be configured by a plurality of devices (devices, computers, or the like), instead. The plurality of devices can cooperatively realize the function of determining the freshness of a fish by communicating with one another.

Figure 23:
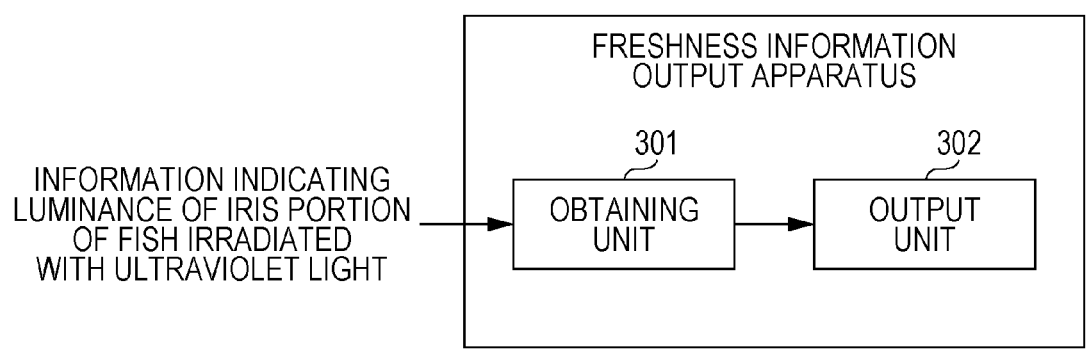
FIG. 23 is a functional block diagram illustrating a freshness information output apparatus according to another embodiment.

In addition, as illustrated in FIG. 23, the freshness information output apparatus may include an obtaining unit 301 that obtains information (for example, an ultraviolet image) indicating the luminance of the iris portion of a fish onto which ultraviolet light is radiated and an output unit 302 that outputs freshness information indicating the freshness of the fish determined on the basis of the foregoing information. The obtaining unit 301 and the output unit 302 are realized by, for example, the computer 14 (refer to FIG. 2). When the function of the determination unit 2 (refer to FIG. 1) is divided into a function of receiving an ultraviolet image and a function of outputting a result of a determination, the obtaining unit 301 corresponds to at least part of the function of receiving an ultraviolet image, and the output unit 302 corresponds to at least part of the function of outputting a result of a determination. The output unit may be realized while including the display 15 (refer to FIG. 2), instead.

In addition, embodiments obtained by modifying the above-described embodiments in various ways that can be easily conceived by those skilled in the art and embodiments realized by arbitrarily combining the components and the functions described in each embodiment are also included in the scope of the present disclosure.

The present disclosure can be used for quantitatively evaluating the freshness of a captured fish before the fish is provided for a consumer market.

What is claimed is:

1. A method for outputting freshness information, the method comprising the steps of:
   obtaining, using a hardware processor, information indicating luminance of an iris portion of an eye of a fish onto which ultraviolet light is radiated; and
   outputting, using the hardware processor, the freshness information indicating freshness of the fish on the basis of the foregoing information.

2. The method according to claim 1, further comprising the steps of:
   capturing an ultraviolet image of the eye of the fish onto which the ultraviolet light has been radiated; and
   extracting a luminance value of the iris portion from the ultraviolet image, determining the freshness of the fish on the basis of the luminance value of the iris portion, and outputting the freshness information.

3. The method according to claim 2,
   wherein, in the step of extracting, a luminance value of a crystalline lens portion is extracted from the ultraviolet image and the freshness of the fish is determined on the basis of a freshness index, which is obtained by normalizing the luminance value of the iris portion using the luminance value of the crystalline lens portion.

4. The method according to claim 3,
   wherein, in the step of extracting, the freshness index is a difference between the luminance value of the iris portion and the luminance value of the crystalline lens portion, a value obtained by dividing the difference by the luminance value of the crystalline lens portion, or a ratio of the luminance value of the iris portion to the luminance value of the crystalline lens portion.

5. The method according to claim 4,
   wherein the step of extracting includes the steps of (a) detecting an edge portion in the ultraviolet image, and (b) detecting a portion similar to a double-circle pattern from the detected edge portion,
   wherein the double-circle pattern includes a first circle and a second circle having a radius larger than that of the first circle,
   wherein a region inside the first circle includes the crystalline lens portion, and
   wherein a region between an arc of the first circle and an arc of the second circle includes the iris portion.

6. The method according to claim 2,
   wherein, in the step of capturing, the ultraviolet image is captured by radiating the ultraviolet light and an infrared image of the eye of the fish is captured by radiating infrared light, and
   wherein, in the step of extracting, the freshness of the fish is determined in accordance with a freshness index, which is obtained by normalizing the luminance value of the iris portion extracted from the ultraviolet image using a luminance value of an iris portion extracted from the infrared image.

7. The method according to claim 6,
   wherein, in the step of extracting, the freshness index is a difference between the luminance value of the iris portion extracted from the ultraviolet image and the luminance value of the iris portion extracted from the infrared image, a value obtained by dividing the difference by the luminance value of the iris portion extracted from the infrared image, or a ratio of the luminance value of the iris portion extracted from the ultraviolet image to the luminance value of the iris portion extracted from the infrared image.

8. The method according to claim 7,
   wherein, in the step of extracting, the freshness of the fish is determined by referring to predetermined determination information, in which each of a plurality of different pieces of freshness information and each of a plurality of ranges of values of the freshness index are associated with each other.

9. The method according to claim 8,
   wherein the freshness information is represented by time elapsed since a fish died, and
   wherein the determination information is information in which a longer time elapsed since a fish died is associated with a range of larger values of the freshness index.

10. A freshness information output apparatus comprising:
    an obtainer that obtains information indicating luminance of an iris portion of an eye of a fish onto which ultraviolet light has been radiated; and
    an outputter that outputs freshness information indicating freshness of the fish determined on the basis of the foregoing information.

11. The freshness information output apparatus according to claim 10, further comprising:
    an ultraviolet light radiator that radiates the ultraviolet light; and
    a mobile information device,
    wherein the mobile information device includes an image capturer that captures an image at a time when the ultraviolet radiator radiates the ultraviolet light and an outputter that determines the freshness of the fish on the basis of a luminance value of the iris portion extracted from the image captured by the image capturer and that displays information indicating a result of the determination.

12. A non-transitory computer-readable recording medium storing a control program for causing a device including a processor to execute a process for determining freshness of a fish, the process comprising the steps of:
    capturing an ultraviolet image of an eye of the fish onto which ultraviolet light has been radiated; and
    extracting a luminance value of an iris portion from the ultraviolet image, determining the freshness of the fish on the basis of the luminance value of the iris portion, and outputting freshness information indicating a result of the determination.

* * * * *